(12) United States Patent
Ban et al.

(10) Patent No.: US 12,365,859 B2
(45) Date of Patent: Jul. 22, 2025

(54) CELL PRODUCTION SYSTEM

(71) Applicants: FANUC CORPORATION, Yamanashi (JP); I PEACE, INC., Palo Alto, CA (US)

(72) Inventors: Kazunori Ban, Yamanashi (JP); Satoshi Kinoshita, Yamanashi (JP); Koji Tanabe, Kyoto (JP); Ryoji Hiraide, Kyoto (JP); Atsushi Nakao, Kyoto (JP)

(73) Assignees: FANUC CORPORATION, Yamanashi (JP); I PEACE, INC., Palo Alto, CA (US)

( * ) Notice: Subject to any disclaimer, the term of this patent is extended or adjusted under 35 U.S.C. 154(b) by 960 days.

(21) Appl. No.: 17/436,074

(22) PCT Filed: Oct. 29, 2019

(86) PCT No.: PCT/JP2019/042414
§ 371 (c)(1),
(2) Date: Sep. 3, 2021

(87) PCT Pub. No.: WO2020/179127
PCT Pub. Date: Sep. 10, 2020

(65) Prior Publication Data
US 2022/0177820 A1 Jun. 9, 2022

(30) Foreign Application Priority Data

Mar. 5, 2019 (JP) ................................ 2019-040036

(51) Int. Cl.
*C12M 3/00* (2006.01)
*C12M 1/00* (2006.01)
(Continued)

(52) U.S. Cl.
CPC ............ *C12M 23/42* (2013.01); *C12M 23/22* (2013.01); *C12M 23/28* (2013.01); *C12M 23/44* (2013.01);
(Continued)

(58) Field of Classification Search
CPC ...... C12M 23/42; C12M 23/22; C12M 23/28; C12M 23/44; C12M 29/04; C12M 41/00;
(Continued)

(56) References Cited

U.S. PATENT DOCUMENTS

2018/0035661 A1* 2/2018 Tanabe ................... C12M 45/22
2018/0072980 A1* 3/2018 Koike .................... C12M 41/46

FOREIGN PATENT DOCUMENTS

DE  102016208552 B3  4/2017
EP      1650291 A1   4/2006
(Continued)

*Primary Examiner* — Basil T. Jos
(74) *Attorney, Agent, or Firm* — HAUPTMAN HAM, LLP

(57) ABSTRACT

This cell production system is provided with: a robot that assists cell production; and a plurality of closed system cell production devices which are affected by the robot in a one-to-many manner, wherein the closed system cell production devices are each provided with a double-sided structure of a dangerous region side affected by the robot and a safe region side on the reverse side of the dangerous region side.

3 Claims, 18 Drawing Sheets

(51) Int. Cl.
    *C12M 1/34*        (2006.01)
    *C12M 1/36*        (2006.01)
(52) U.S. Cl.
    CPC ............ *C12M 29/04* (2013.01); *C12M 41/00*
                (2013.01); *C12M 41/36* (2013.01)
(58) Field of Classification Search
    CPC ...... C12M 41/36; C12M 23/50; C12M 23/52;
                        C12M 41/48; C12M 23/58
    See application file for complete search history.

(56) References Cited

FOREIGN PATENT DOCUMENTS

| | | |
|---|---|---|
| EP | 1900806 A1 | 3/2008 |
| EP | 2482079 A2 | 8/2012 |
| JP | 2006115798 A | 5/2006 |
| JP | 2006149268 A | 6/2006 |
| JP | 2007275030 A | 10/2007 |
| JP | 200854690 A | 3/2008 |
| JP | 2008147202 A | 6/2008 |
| JP | 2008533989 A | 8/2008 |
| JP | 2008237046 A | 10/2008 |
| JP | 2008237112 A | 10/2008 |
| JP | 4183742 B1 | 11/2008 |
| JP | 2009502168 A | 1/2009 |
| JP | 2009219415 A | 10/2009 |
| JP | 2009291104 A | 12/2009 |
| JP | 2012147685 A | 8/2012 |
| JP | 2013508673 A | 3/2013 |
| JP | WO2012098931 A1 | 6/2014 |
| JP | 2016-124057 A | 7/2016 |
| JP | 2016185584 A | 10/2016 |
| JP | WO2016170623 A1 | 10/2017 |
| JP | WO2016147897 A1 | 12/2017 |
| JP | WO2016147898 A1 | 12/2017 |
| JP | 201820 A | 1/2018 |
| JP | 201819685 A | 2/2018 |
| JP | 2018510660 A | 4/2018 |
| JP | 2018512889 A | 5/2018 |
| JP | 2018516591 A | 6/2018 |
| JP | 2018117586 A | 8/2018 |
| WO | 2004091746 A2 | 10/2004 |
| WO | 2006/102416 A2 | 9/2006 |
| WO | 2006104445 A1 | 10/2006 |
| WO | 2007001002 A1 | 1/2007 |
| WO | WO-2017079682 A1 * | 5/2017 .............. C12M 1/22 |
| WO | 2017174298 A1 | 10/2017 |

* cited by examiner

SHUTTLE ARRIVAL

SLIDER EXTENSION

I Plate RECEPTION COMPLETE

SHUTTLE MOVEMENT

SHUTTLE ARRIVAL

I Plate RECEPTION COMPLETE

SHUTTLE MOVEMENT

CELL PRODUCTION SYSTEM

RELATED APPLICATIONS

The present application is a National Phase of International Application No. PCT/JP2019/042414 filed Oct. 29, 2019, which claims priority to Japanese Application No. 2019-040036, filed Mar. 5, 2019.

FIELD

The present invention relates to cell production technology, and especially to a cell production system that ensures biological and physical safety and is also suitable for mass production.

BACKGROUND

Embryonic stem cells (ES cells) are stem cells established from the early embryo of a human or mouse, and they have pluripotency allowing them to differentiate into all cells present in the body. Human ES cells are considered to be usable in cell transplantation treatment for numerous diseases including Parkinson's disease, juvenile onset diabetes and leukemia.

However, similar to organ transplantation, transplantation of ES cells is associated with the problem of eliciting rejection. Moreover, many dissenting opinions have been raised from an ethical viewpoint against the use of ES cell lines that have been established by destruction of human embryos.

Prof. Shinya Yamanaka of Kyoto University succeeded in transferring the four genes: Oct3/4, Klf4, c-Myc and Sox2 into somatic cells, establishing induced pluripotent stem cells (iPS cells), and for that he received the 2012 Nobel Prize in Physiology or Medicine (see patent literature 1, for example). As ideal pluripotent cells free of the problem of rejection or ethical issues, iPS cells are expected to be useful in cell transplantation treatment.

Induced stem cells such as iPS cells are established by transferring inducing factors such as genes into cells which are then subjected to amplifying culturing and cryopreservation. However, in order to create iPS cells for clinical use (GLP or GMP grade), for example, it is necessary to use a cleanroom kept in a highly uncontaminated state, incurring high cost for maintenance. This has presented a problem for industrialization in terms of how to increase efficiency and reduce costs for operation of the cleanroom.

Moreover, creation of iPS cells is considerably dependent on manual operation and few technicians with the ability to create iPS cells for clinical use are available. Another problem is that the series of operations from establishment of stem cells to their storage are complex. Culturing of cells for clinical use requires three steps: confirming Standard Of Process (SOP), manipulation according to SOP and confirmation of presence or absence according to SOP, and it is highly unproductive for these steps to be carried out by human operators. Cell culturing also requires 24-hour management, and since preservation of stem cells lasts for periods of many decades there has been a limit to management by human resources alone.

Totally-enclosed cell production devices have been developed (see patent literature 2, for example), that do not require highly uncontaminated cleanrooms and can be operated in normal controlled areas (for example, where either the microorganisms and microparticles are grade D level or higher based on the WHO-GMP standard). In order to avoid employing human resources and to automate the complex steps of cell production, cell production systems have also been developed that comprise robots which aid in cell production. The publications listed below are well known as prior art for such cell production systems. However, none of the publications employ closed cell production devices that can be operated in a normal controlled area.

Patent literatures 3 to 9 disclose automatic cell culturing apparatuses having operation robots disposed in a cleanroom, and patent literature 10 discloses an automatic cell subculturing system with a rotating robot inside a processing station.

Patent literature 11 discloses an automatic cell culture facility comprising a plurality of cell culture chambers, a raw material processing chamber and a robot that conducts cell transport between product processing chambers, and patent literature 12 discloses a robot that operates at least a portion of one or more of a plurality of cell cultures.

Patent literatures 13 and 14 each disclose a cell culture processing system comprising a closed space in which a conveying apparatus that includes a transfer robot, and different processing devices, can be sterilized and decontaminated, with linkage between them being possible by detachable means.

Patent literature 15 discloses a sample storage device comprising an electric robot that transports a sample container such as a cell culture flask, and Patent literature 16 discloses a robot system that opens and closes cell culturing vessels using a robotic hand.

Patent literature 17 discloses an automatic cell culturing apparatus comprising a robot that moves while irradiating ultraviolet light, and Patent literatures 18 to 20 disclose cell culture incubators comprising an object-moving robot.

Patent literatures 21 to 22 disclose production apparatuses for cultured cell products, comprising a first robotic arm that moves a cell culturing vessel to an observation location and a second robotic arm that transfers cells in the cell culturing vessel to a product container.

Patent literature 23 discloses a cell culturing system comprising a plurality of devices used for cell culturing, a robot that conducts cell culturing, a housing section that houses the plurality of devices and the robot, and a door provided in the side wall of the housing section.

CITATION LIST

Patent literature 1: Japanese Patent Publication No. 4183742
Patent literature 2: Japanese Unexamined Patent Publication No. 2018-019685
Patent literature 3: Japanese Unexamined Patent Publication No. 2006-115798
Patent literature 4: Japanese Unexamined Patent Publication No. 2006-149268
Patent literature 5: Japanese Unexamined Patent Publication No. 2007-275030
Patent literature 6: Japanese Unexamined Patent Publication No. 2008-054690
Patent literature 7: Japanese Unexamined Patent Publication No. 2008-237046
Patent literature 8: Japanese Unexamined Patent Publication No. 2008-237112
Patent literature 9: Japanese Unexamined Patent Publication No. 2009-291104
Patent literature 10: Japanese Patent Public Inspection No. 2008-533989
Patent literature 11: Japanese Unexamined Patent Publication No. 2009-219415

Patent literature 12: Japanese Patent Public Inspection No. 2009-502168
Patent literature 13: Japanese Unexamined Patent Publication No. 2012-147685
Patent literature 14: Domestic Re-publication of PCT International Application No. 2012/098931.
Patent literature 15: Japanese Patent Public Inspection No. 2013-508673
Patent literature 16: Japanese Unexamined Patent Publication No. 2018-000020
Patent literature 17: Japanese Unexamined Patent Publication No. 2018-117586
Patent literature 18: Japanese Patent Public Inspection No. 2018-510660
Patent literature 19: Japanese Patent Public Inspection No. 2018-512889
Patent literature 20: Japanese Patent Public Inspection No. 2018-516591
Patent literature 21: Domestic Re-publication of PCT International Application No. 2018/147897.
Patent literature 22: Domestic Re-publication of PCT International Application No. 2018/147898.
Patent literature 23: Domestic Re-publication of PCT International Application No. 2016/170623.

SUMMARY

Technical Problem

With an automatic cell production system using a closed cell production device it is possible to produce cells in a normally controlled area, but to lower the risk of unwanted contamination it is desirable to prevent entry of humans into the cell production areas. Moreover, since the timing and manner of operation of some robots in the cell production area cannot be foreseen during system operation, it is necessary to isolate humans from the cell production area in order to ensure safety.

Because cultured cells are alive and can die if not appropriately delivered, treated and stored at the proper times, the cell production system must be continuously operated 24 hours a day without stopping, which also requires personnel-attended areas to deal with potential troubles with the closed cell production device.

Due to variation in the products themselves, unlike manufacturing industries in other fields, the levels of cell production by different closed cell production devices is different. Another problem, therefore, is that they are not suited for mass production by system control following a fixed flow.

There is a need for a cell production system that ensures biological and physical safety while also being suited for mass production.

Solution to Problem

One aspect of the present disclosure provides a cell production system comprising a robot that assists in cell production and a plurality of closed cell production devices which are affected by the robot in a one-to-many manner, wherein the closed cell production devices each comprise a double-sided structure with a hazardous area side in which the robot operates and a safe area side on the side opposite from the hazardous area side.

Another aspect of the disclosure provides a cell production system comprising a robot that assists in cell production, a plurality of closed cell production devices which are affected by the robot in a one-to-many manner, and a computer system which has a plurality of closed cell production device tasks to be executed in parallel, and a robot task in communication with the plurality of closed cell production device tasks in a many-to-one manner, wherein the robot task activates at least one program module from among a plurality of different robot program modules in response to requests by the plurality of closed cell production device tasks.

Yet another aspect of the disclosure provides a cell production system comprising a robot that assists in cell production, a cell surrounding the robot, and a plurality of closed cell production devices which are attached to the cell and are affected by the robot in a one-to-many manner, wherein the closed cell production devices can be accessed by the robot from inside the cell and can be maintained from outside the cell.

Yet another aspect of the disclosure provides a cell production system comprising a robot that assists in cell production, a wall structure parallel to a line on which the robot is self-propelled, and a plurality of closed cell production devices which are attached to the wall structure and are affected by the robot in a one-to-many manner, wherein the closed cell production devices can be accessed by the robot from the front side of the wall structure and can be maintained from the back side of the wall structure.

Yet another aspect of the disclosure provides a cell production system comprising a robot that assists in cell production, a plurality of closed cell production devices which are affected by the robot in a one-to-many manner, and a shuttle that is able to transport the closed cell production devices between the robot stationing location and the closed cell production device storage location, wherein the shuttle can access the closed cell production devices from the front side of the wall structure provided in the storage location and can maintain them from the back side of the wall structure provided in the storage location.

Advantageous Effects of Invention

According to one aspect of the disclosure it is possible to provide a cell production system comprising a double-sided structure in which closed cell production devices have a hazardous area side and a safe area side, and which is therefore biologically and physically safe. It is also possible to provide a cell production system suited for mass production by on-demand system control, even when levels of cell production vary for different closed cell production devices. The maintenance system is also reinforced depending on the type of equipment structure.

DESCRIPTION OF EMBODIMENTS

Figure 1:
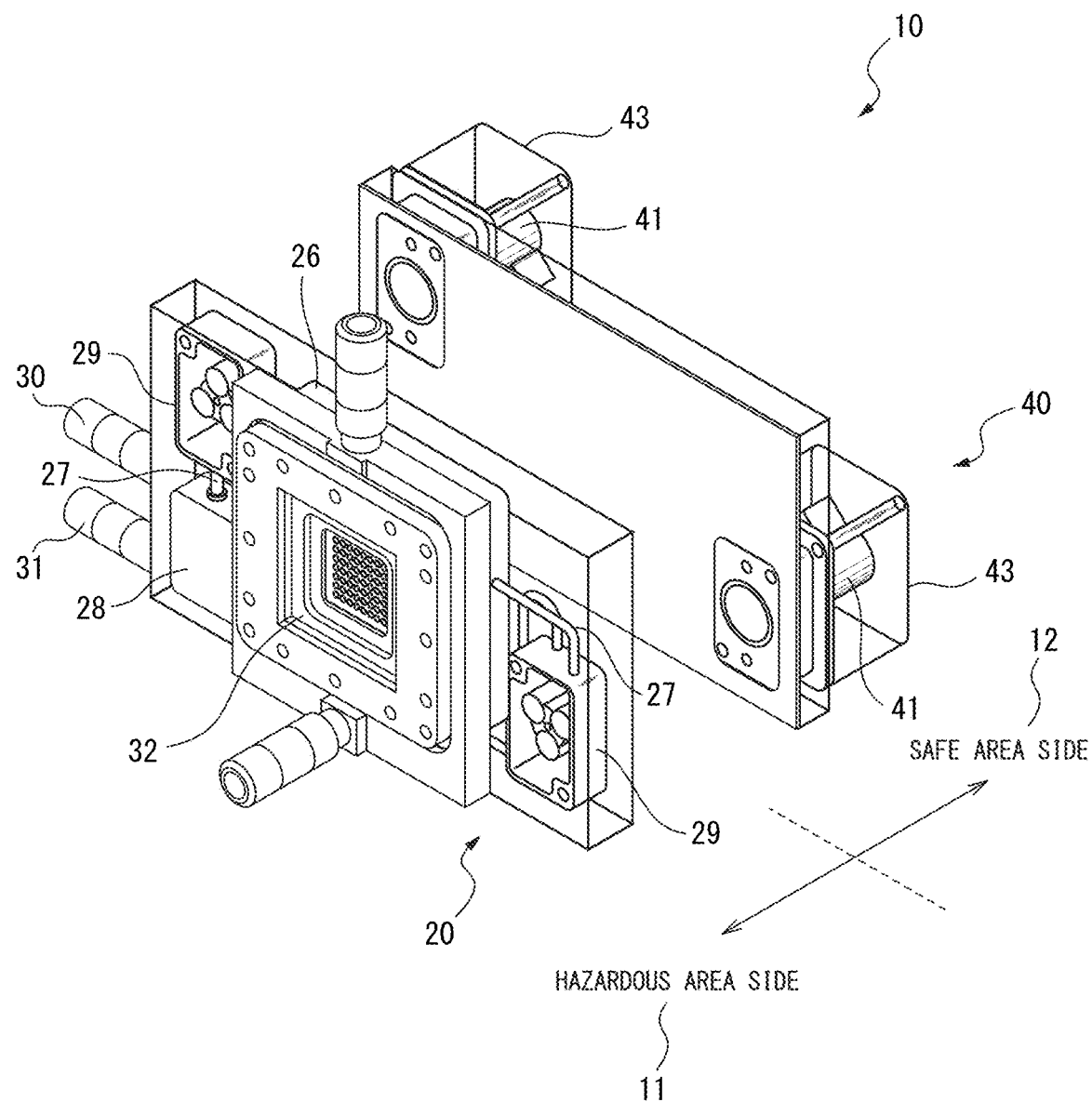
FIG. 1 is a partial exploded view of a closed cell production device according to one embodiment.

Embodiments of the disclosure will now be explained in detail with reference to the accompanying drawings. In the drawings, same or similar constituent elements will be indicated by the same or similar reference numerals. The embodiments described below do not limit the technical scope of the invention as laid out in the claims, or the definitions of terms.

1. Closed Cell Production Device

Figure 2:
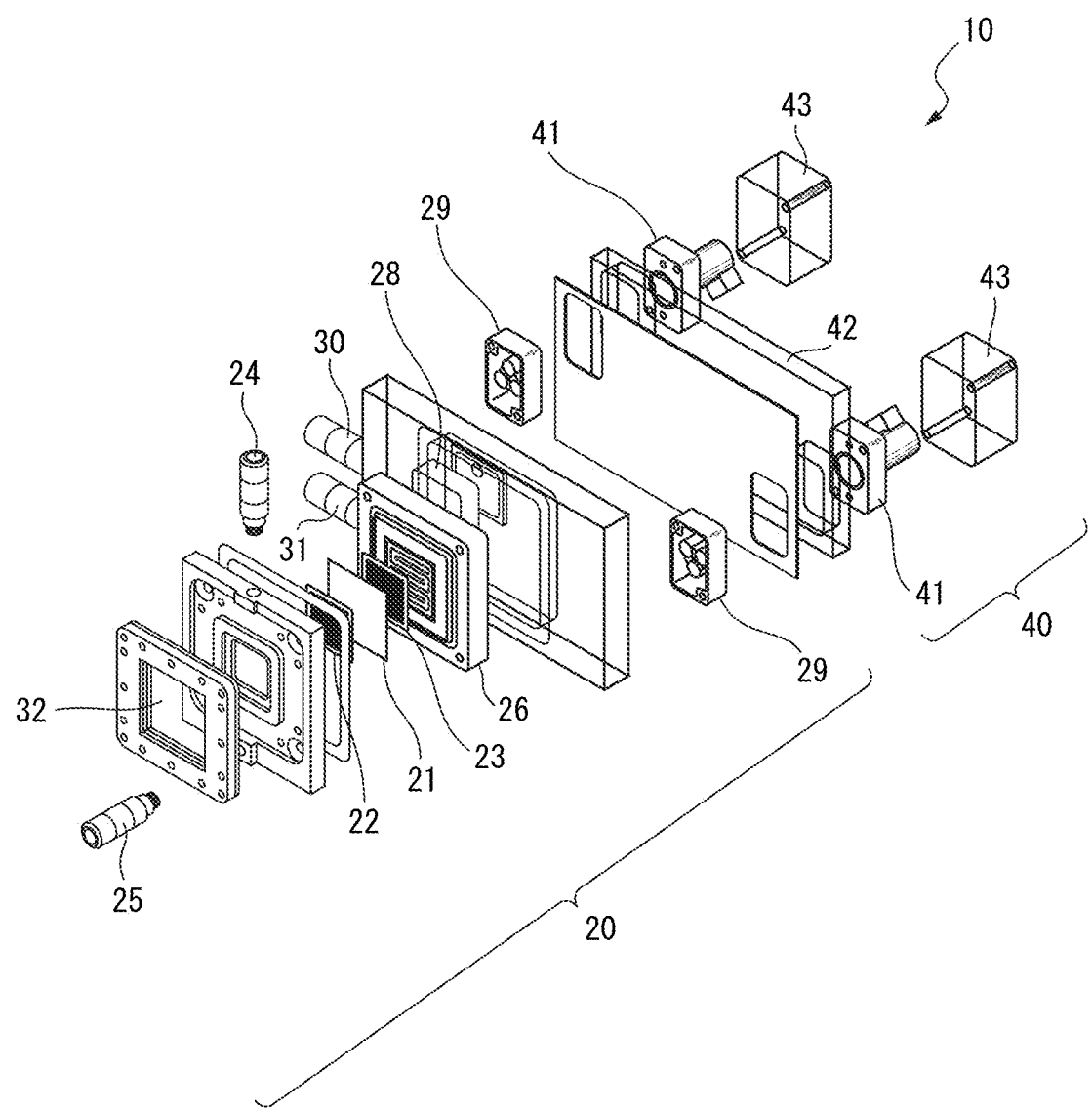
FIG. 2 is an exploded view of a closed cell production device according to one embodiment.

FIG. 1 and FIG. 2 each show a closed cell production device 10 according to the present embodiment. The closed cell production device 10 is a closed cell converter that carries out cell initialization and reprogramming, fate switching and transformation, including transformation from somatic cells to stem cells and transformation from somatic cells to target cells. It should be noted, however, that the closed cell production device 10 may also be a device that only carries out cell culturing or amplifying culturing.

The closed cell production device 10 is a cell production device that internally aggregates all of the portions to be highly cleaned, and that can be used in normally controlled areas.

The closed cell production device 10 has a double-sided structure with a hazardous area side 11 that is affected by the robot and a safe area side 12 on the opposite side from the hazardous area side. It therefore has a system structure with the robot and closed cell production devices in a one-to-many relationship even when the closed cell production devices 10 are provided as fixed installations. The closed cell production devices 10 can therefore interact with the robot in a fixed direction at all times without needing to rotate or move the target operating closed cell production device 10.

Each closed cell production device 10 comprises a cell production cartridge 20 and a driving base 40 that drives the cartridge 20. The front of the cartridge 20 is disposed facing the hazardous area side 11 that is affected by the robot, and the back side of the driving base 40 is disposed facing the safe area side 12 which is the opposite side from the hazardous area side 11. From the viewpoint of preventing biological contamination, the cartridge 20 is disposable while the driving base 40 is reusable, to help lower the construction cost for the closed cell production device 10. However, the cartridge 20 may be reused so long as it is maintained in a highly clean state by cleaning with cleaning fluid or by heat sterilization, gamma sterilization or ultraviolet sterilization. The cartridge 20 is removable from the driving base 40 with the back side of the cartridge 20 being connected to the front side of the driving base 40. The closed cell production device 10 has a structure allowing it to be maintained from the safe area side 12.

The cartridge 20 is constructed so as to carry out at least one of the following cell production steps: separation of inducing cells from somatic cells of the blood or skin, induction of differentiation, amplifying culturing, cell mass fragmentation and target cell recovery. The cartridge 20 for this example comprises a culture component permeating member 21, a culture side plate 22 that contacts with one side of the culture component permeating member 21, and a culture medium side plate 23 that contacts with the other side of the culture component permeating member 21. The cartridge 20 comprises a culture side supply plug 24 for supply of fluid to the culture side plate 22 through different fluid storage tanks (not shown), and a culture side discharge plug 25 for discharge of fluid from the culture side plate 22. The culture side supply plug 24 is connected to a fluid feeder such as a syringe, vial or infusion bag (not shown) housing a fluid such as blood, pluripotent inducing factor or culture reagent, while the culture side discharge plug 25 is connected to a fluid discharger such as a syringe, vial or infusion bag (not shown) housing a fluid such as a sample of the cell mass suspension during production, or the cell mass suspension after production.

The cartridge 20 also comprises a culture medium holding layer 26 that holds the culture medium side plate 23, a culture medium tank 28 connected to the culture medium holding layer 26 through a culture medium channel 27, and two fluid machines 29 such as pumps disposed in the culture medium channel 27. The cartridge 20 further comprises a culture medium side supply plug 30 connected to a fluid feeder (not shown) housing unused culture medium, and a culture medium side discharge plug 31 connected to a fluid discharger (not shown) housing used culture medium. Although the culture medium side supply plug 30 and culture medium side discharge plug 31 are mounted on the side wall of the culture medium tank 28 in this example, they may instead be mounted on the front of the culture medium tank 28, but in either case they are robot-manipulated. The different plugs mentioned above only need to be connectors that ensure a closed system, and they may be needle connectors or needleless connectors. The different fluid feeders and fluid dischargers mentioned above preferably comprise fluid machinery such as pumps.

The cartridge 20 also comprises a window 32 allowing observation of the cell production step by a sensor such as a camera, from the hazardous area side 11. The sensor may be provided near the robot end-effector or connected to the cartridge 20. The window 32 is formed of a transparent resin or quartz glass comprising a transparent conductive film, for example, and a temperature control unit (not shown) is connected to it. The temperature control unit keeps the temperature in the cartridge 20 at a predetermined culturing temperature.

The driving base 40 comprises two driving units 41 each with a motor and piezo element, a drive holding member 42 that holds the driving units 41, and two outside air blocking members 43 covering the driving units 41. The driving units 41 respectively drive the two fluid machines 29 inside the cartridge 20. The driving units 41 can be maintained by removing the outside air blocking members 43 for the drive holding member 42. Removal of the driving units 41 also allows the fluid machines 29 of the cartridge 20 to be maintained. Alternatively, as described below, the construction may be such as to allow removal of the closed cell production devices 10 which each comprise a cartridge 20 and driving base 40, out toward the safe area side 12 as necessary, to allow maintenance of the entirety.

2. Construction of Cell Production System

The cell production system carries out cell production in a normal controlled area without requiring a highly uncontaminated cleanroom, but in order to counter potential rupture of the closed system, the cell production area may be adjusted to positive pressure. Although the environment is a normal environment, it is assumed to be without the presence or intervention of humans in the cell production area during system operation in order to lower the risk of unwanted contamination and other problems.

In the cell production area, the cell production system comprises a robot that assists in cell production and a plurality of closed cell production devices that are affected by the robot in a one-to-many manner. In a normal environment, handling, transport and attachment/detachment of materials is carried out by a robot to increase the stability of work quality. This eliminates the misunderstandings or work errors that may often occur with manual operation, while the execution results of robot programs can also be recorded to leave a recorded work history. The type of equipment configuration used in a cell production system may be a cell-type, line-type or shuttle-type system, for example. These equipment configurations will now be described in order.

2-1. Cell-Type

Figure 3:
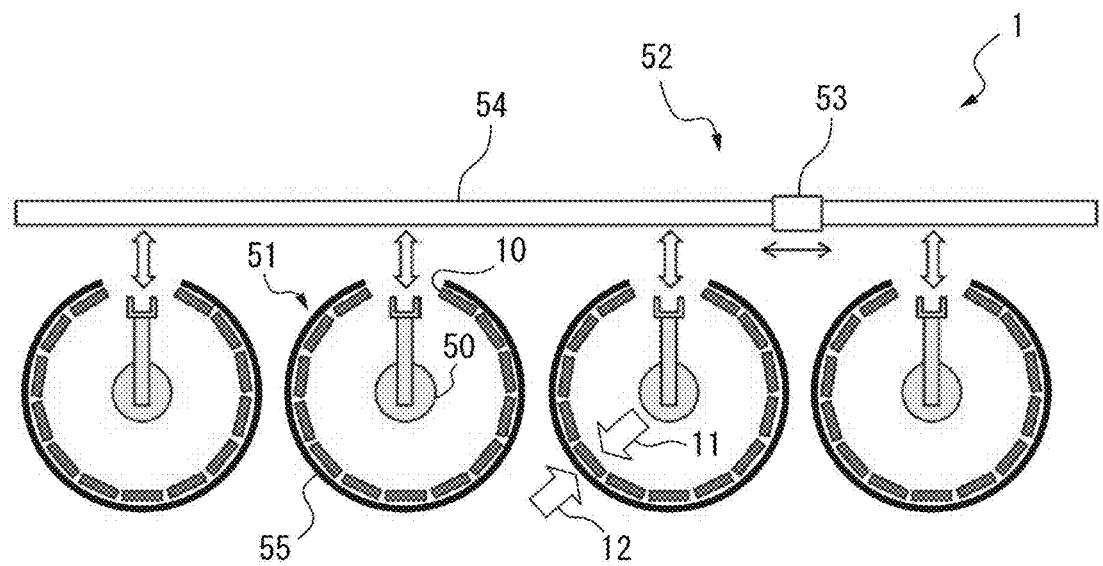
FIG. 3 is a plan view showing an example of a cell-type cell production system.

FIG. 3 shows an example of a cell-type cell production system 1. The cell production system 1 is a cell-type production system comprising a robot 50 that assists in cell production, a cell 51 that surrounds one robot 50, and a plurality of closed cell production devices 10 that are mounted in the cell 51 and are affected by the robot 50 in an one-to-many manner. Types of robots for this robot 50 include industrial robots such as vertically articulated robots and horizontally articulated robots. The cell 51 has a wall structure 55 which is polygonal or circular, with a plurality of closed cell production devices 10 disposed in the wall structure 55 of the cell 51. The wall structure 55 of the cell 51 may spatially separate the hazardous area side 11 and the safe area side 12. The plurality of closed cell production devices 10 in FIG. 3 are drawn on one level on the plane, but they may also be disposed on different levels in the vertical direction of the page.

The cell production system 1 may also comprise a plurality of linked cells 51, with a material transport mechanism 52 provided in coupled connection with each cell 51. The material transport mechanism 52 may be a shuttle 53 that travels between the material stationing location and each cell 51. The shuttle 53 may be a self-propelled shuttle or robot traveling on a travel axis rail 54, but may also be an automated guided vehicle (AGV) or drone. The material transport mechanism 52 may also be a simple belt conveyor. The cell 51 may also be disposed on both sides instead of only one side of the travel axis rail 54. The robot 50 carries a material such as a cell production cartridge, syringe, vial or infusion bag into the cells 51, removes and attaches cartridges onto the driving base and removes and attaches a fluid feeder or fluid discharger onto the cartridges, while also carrying used materials out of the cells 51.

The closed cell production device 10 allows access to the robot 50 from inside the wall structure 55 of each cell 51 and allows maintenance from outside the wall structure 55 of each cell 51. The wall structure 55 also performs a "safety fence" function for the robot 50. This allows maintenance workers to remain isolated from the robot 50 when the maintenance workers enter the area outside of the cells 51, thus helping to ensure physical safety. Since maintenance workers do not enter the area inside the cells 51 during operation of the cell production system 1, biological contamination can be prevented. When a particular problem has occurred in the closed cell production device 10, it is possible to maintain only the closed cell production device 10 in which the problem has occurred, from outside the cell 51, even while the system is still operating.

Figure 4A:
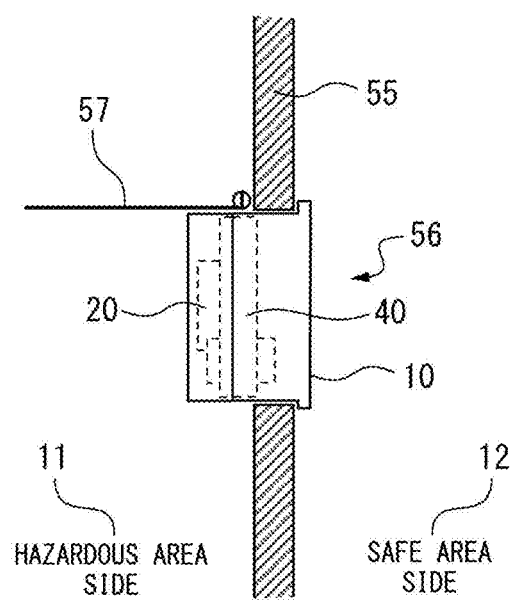
FIG. 4A is a partial cross-sectional view showing an example of the construction of a closed cell production device being removed toward the safe area side.
Figure 4B:
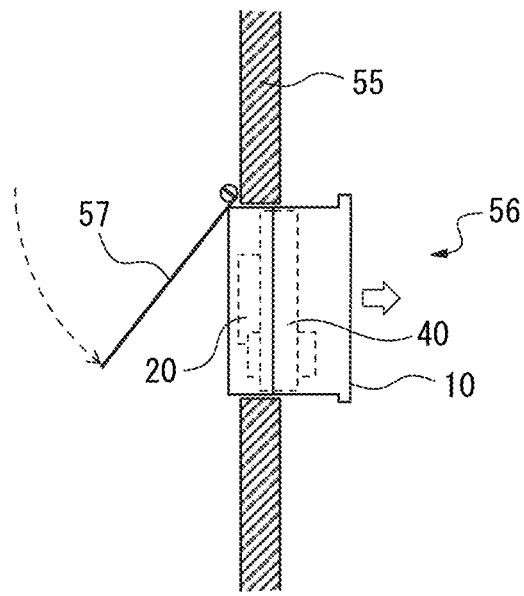
FIG. 4B is a partial cross-sectional view showing an example of the construction of a closed cell production device being removed toward the safe area side.
Figure 4C:
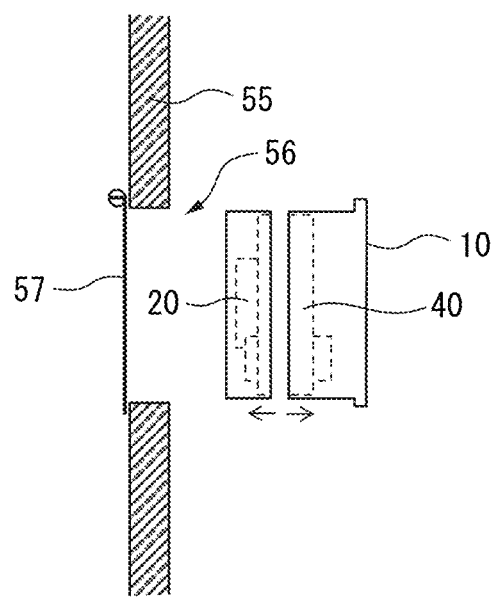
FIG. 4C is a partial cross-sectional view showing an example of the construction of a closed cell production device being removed toward the safe area side.

FIG. 4A to FIG. 4C depict the configuration of a closed cell production device 10 comprising a cartridge 20 and a driving base 40, as it is being removed to the safe area side 12. The wall structure 55 comprises an opening 56 in which the closed cell production device 10 can be placed, and a shutter 57 that can be moved by a hinge between an open position and a closed position. When the closed cell production device 10 is inserted into the opening 56 as shown in FIG. 4A, the shutter 57 is flipped upward by forward movement of the closed cell production device 10 and moved to the open position, while the closed cell production device 10 causes the opening 56 to be in a closed state. When the closed cell production device 10 is removed out from the opening 56 as shown in FIG. 4B, the shutter 57 falls down due to retraction of the closed cell production device 10, moving to the closed position, with the shutter 57 thus bringing the opening 56 to a closed state. This allows maintenance to be carried out with the spaces on the hazardous area side 11 and safe area side 12 automatically isolated from each other. During maintenance as shown in FIG. 4C, the closed cell production device 10 may separated into the cartridge 20 and driving base 40.

2-2. Line-Type

Figure 5:
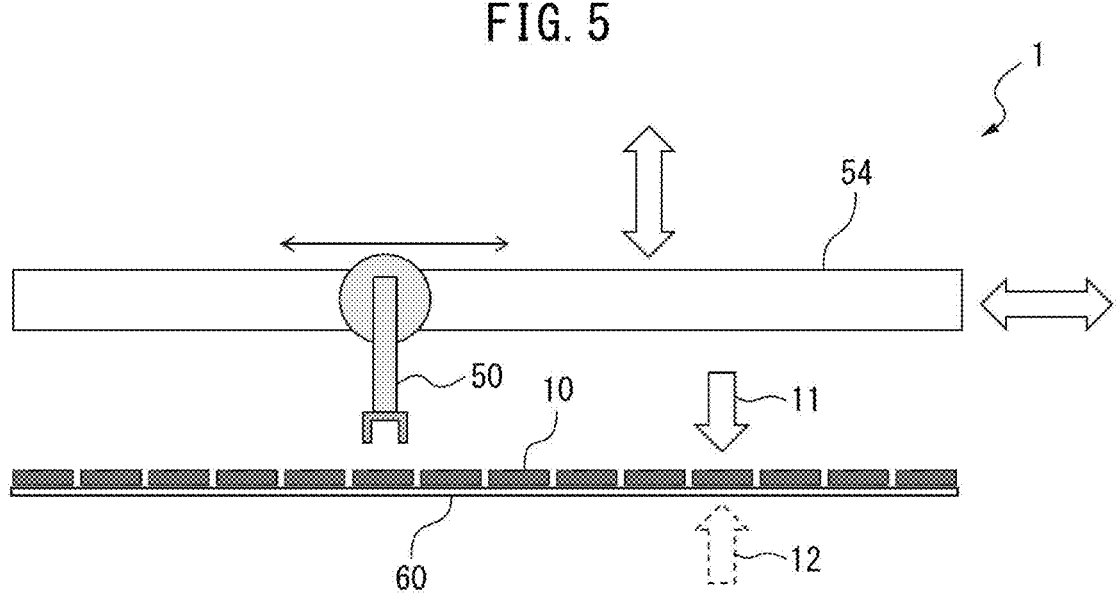
FIG. 5 is a plan view showing an example of a line-type cell production system.

FIG. 5 shows an example of a line-type cell production system 1. The cell production system 1 is a line-type production system comprising a robot 50 that assists in cell production, a wall structure 60 parallel to a travel axis rail 54 on which the robot 50 is self-propelled, and a plurality of closed cell production devices 10 that are mounted on the wall structure 60 and are affected by the robot 50 in an one-to-many manner A plurality of closed cell production devices 10 are disposed on the wall structure 60. The wall structure 60 may be a grid-like safety fence, but it may also have a structure that spatially separates the hazardous area side 11 and safe area side 12. The plurality of closed cell production devices 10 in FIG. 5 are drawn on one level on the plane, but they may alternatively be disposed on different levels in the vertical direction of the page. The closed cell production devices 10 may also be disposed on both sides of the travel axis rail 54 instead of only one side.

Here the robot 50 is self-propelled along a relatively long distance, but a plurality of robots may also be provided on the travel axis rail 54. Alternatively, the construction may have a gantry incorporated with a separate vertically inverted travel axis rail situated at a high location, with the robot mounted on a ceiling-suspended traveling platform. This will free the floor surface of the manufacturing plant to allow more effective use of the floor surface area as a location for supply or transport of materials, for example.

When the number of closed cell production devices 10 serviced by a single robot 50 is increased, a line-type allows the number of closed cell production devices installed for each robot to be increased more easily than the cell-type described above. In addition, since a line-type provides a wider range of movement for the robot 50, the robot 50 can retrieve materials and transport used materials out of the system. Supply and transport of materials does not necessarily require the materials themselves to be moved to the necessary location as with a cell-type.

The closed cell production device 10 allows access to the robot 50 from the front side of the wall structure 60 and allows maintenance from the back side of the wall structure 60. This can ensure physical and biological safety, similar to a cell-type. It also allows maintenance of only the closed cell production device 10 in which a problem has occurred, from the back side of the wall structure 60, even while the system is operating.

2-3. Shuttle-Type

Figure 6:
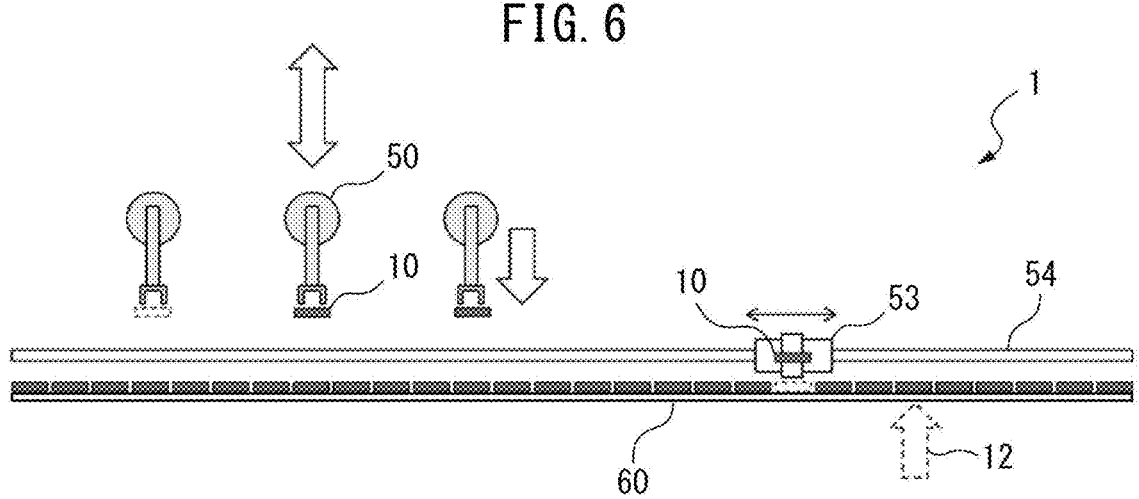
FIG. 6 is a plan view showing an example of a shuttle-type cell production system.
Figure 7A:
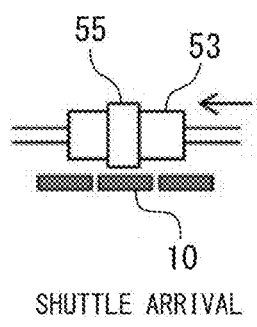
FIG. 7A is a plan view showing the state of a shuttle receiving a closed cell production device.
Figure 7B:
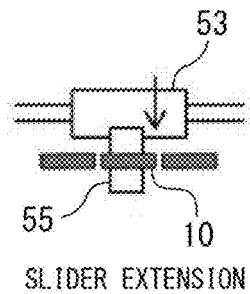
FIG. 7B is a plan view showing the state of a shuttle receiving a closed cell production device.
Figure 7C:
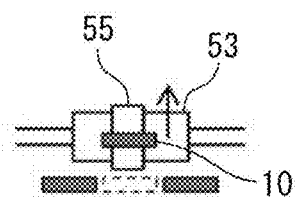
FIG. 7C is a plan view showing the state of a shuttle receiving a closed cell production device.
Figure 7D:
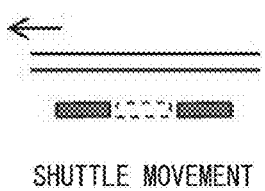
FIG. 7D is a plan view showing the state of a shuttle receiving a closed cell production device.

FIG. 6 shows an example of a shuttle-type cell production system 1. The cell production system 1 is a shuttle-type production system comprising a robot 50 that assists in cell production, a plurality of closed cell production devices 10 that are affected by a robot 50 in an one-to-many manner, and a shuttle 53 that can transport the closed cell production devices 10 between the stationing location of the robot 50 and the storage locations of the closed cell production devices 10. A shuttle-type system differs from a line-type in that the robot 50 is not self-propelled, but rather the closed cell production devices 10 are transported by the shuttle 53 between the stationing location of the robot 50 and the storage locations of the closed cell production devices 10. A wall structure 60 is provided in the storage location of the closed cell production devices 10, where the plurality of closed cell production devices 10 are disposed. The wall structure 60 may also be a grid-like safety fence, but it may also have a structure that spatially separates the hazardous area side and safe area side. Here the plurality of closed cell production devices 10 in FIG. 6 are drawn on one level on the plane, but they may also be disposed on different levels in the vertical direction of the page.

When the number of closed cell production devices 10 serviced by a single robot is greater than in a line-type, the system structure may have one or more robots 50 stationed in a fixed manner and may employ a shuttle 53 for transporting the closed cell production devices 10. The shuttle 53 may travel on the travel axis rail 54, or it may be an AGV or a drone. When a shuttle-type is employed, however, the closed cell production devices 10 (each a combination of a cell production cartridge and driving base) must operate in a stand-alone manner. For example, each closed cell production device 10 preferably comprises an input/output interface and wireless communication interface, including a CPU, a memory, a bus and peripheral devices (such as a pump and sensor), and is driven by a battery while being in wireless communication with host computer equipment that controls and manages the system as a whole, thereby interacting with commands relating to cell production and information relating to the state of production.

Basic operation of a shuttle-type system is as follows. The plurality of aligned closed cell production devices 10 are each operated independently in their storage location, with their respective production steps for cell production progressing independently. When the closed cell production devices 10 are in need of intervention such as carrying in or out of materials or observation with a sensor, the request is sent to the host computer equipment and a command from the host computer equipment causes the shuttle 53 to retrieve a closed cell production device 10 from the storage location for the closed cell production device 10. The shuttle 53 mounts the closed cell production device 10 and moves to the stationing location of the robot 50. The robot 50 receives the closed cell production device 10 from the shuttle 53 and carries out the necessary intervention. During the intervention, the shuttle 53 may also move to a different location and carry out different processing. Once the robot 50 has completed intervention for the closed cell production device 10, the shuttle 53 again moves in front of the robot 50 and the closed cell production device 10 is reinserted into the shuttle 53. The shuttle 53 then transports the closed cell production device 10 and returns the closed cell production device 10 to its original position in the storage location.

FIG. 7A to FIG. 7D are plan views showing the state of a shuttle 53 receiving a closed cell production device 10. The shuttle 53 moves near a target closed cell production device 10 situated in its storage location (see FIG. 7A). The shuttle 53 comprises a slider 55, the slider 55 extending to the closed cell production device 10 side to grip the closed cell production device 10 (see FIG. 7B). Returning the extended slider 55 to its original position causes the closed cell production device 10 to move onto the shuttle 53 (see FIG. 7C). The shuttle 53 then travels on the travel axis rail 54 (see FIG. 7D).

Figure 8A:
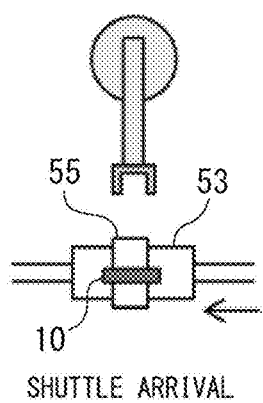
FIG. 8A is a plan view showing the state of a shuttle delivering a closed cell production device to a robot stationing location.
Figure 8B:
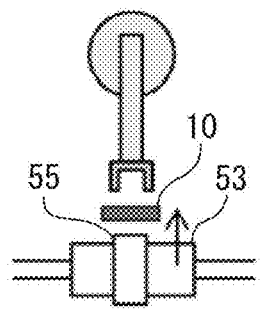
FIG. 8B is a plan view showing the state of a shuttle delivering a closed cell production device to a robot stationing location.
Figure 8C:
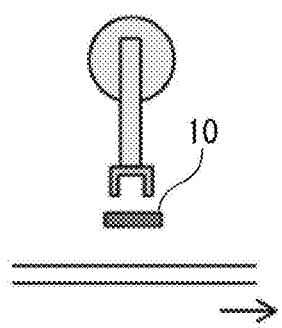
FIG. 8C is a plan view showing the state of a shuttle delivering a closed cell production device to a robot stationing location.

FIG. 8A to FIG. 8C are plan views showing the state of a shuttle 53 delivering a closed cell production device 10 to the stationing location of a robot 50. The shuttle 53 moves near to the robot 50 (see FIG. 8A). The robot 50 extends its arm to grip the closed cell production device 10 situated on the shuttle 53, and transports the closed cell production device 10 to a jig stationed near the robot 50 (see FIG. 8B). The shuttle 53 on which the closed cell production device 10 is no longer situated then moves from the stationing location of the robot 50 for different processing (see FIG. 8C). At the same time, intervention into the closed cell production device 10 by the robot 50 begins.

Each of the closed cell production devices 10 has a fluid feeder and fluid discharger connected as appropriate as the cell production steps progress, which are removed from the closed cell production device 10 when no longer needed, such operations being carried out when the closed cell production device 10 is stationed at the jig (not shown) situated near the robot 50 (see FIG. 8C). Supply of materials for the robot 50 may be carried out from the side opposite the closed cell production device 10 with respect to the robot 50 in FIG. 8C.

The closed cell production devices 10 can be accessed by the shuttle 53 from the front side of the wall structure 60 provided at the storage location, and can be maintained from the back side of the wall structure 60 provided at the storage location. This can ensure physical and biological safety, similar to a cell-type or line-type system. It also allows maintenance of only the closed cell production device 10 in which a problem has occurred, from the back side of the wall structure 60 provided at the storage location, even while the system is operating.

3. Operation of Cell Production System

An example of operation of a cell production system in a cell production area will now be described.

(1) Confirming State of Driving Base by Sensor

The state of the driving base 40 is confirmed using a first sensor (such as a camera, proximity sensor or three-dimensional visual sensor) mounted near an end-effector of the tip of the arm of the robot 50. The state of the driving base 40 includes, for example, whether or not unnecessary elements are mounted on the driving base 40, or whether the fastener of the driving base 40 anchoring the cartridge 20 is open.

(2) Mounting of Cartridge onto Driving Base

The robot 50 holds an unused cartridge 20 at the supply location while mounting it on the target driving base 40. Just before gripping, a first sensor is used to measure the position and posture of the cartridge 20 at the supply location, while the first sensor is also used to measure the position and posture of the driving base 40 using the first sensor just before mounting, thus allowing correction of the previously taught target position and posture of the robot 50 at the target location. This allows the robot 50 to carry out accurate gripping and mounting even when the cartridge 20 is not precisely positioned. Since this also eliminates the need for a special mechanism to position the cartridge 20, it allows the system configuration to be greatly simplified. It can also help significantly reduce prior notification operations in the robot operation program.

For notification of a target position of a robot in a teaching/playback system that does not use a sensor, if the system has 100 locations for the driving base 40 then at most it becomes necessary to make 100 pre-notifications. When employing a system that performs calibration of the target position by a sensor, however, it becomes possible to properly mount cartridges 20 on driving bases 40 at the 100 locations by simply making one pre-notification, in the best case scenario.

By providing a force sensor at the root section of the end-effector of the robot 50, or providing a torque sensor at each joint of the robot, it is possible to effect force control (compliance control) on the robot 50, so that when the cartridge 20 being gripped by the robot 50 is mounted on the driving base 40, the destination of the robot 50 can be corrected so that the cartridge 20 and driving base 40 follow each other even with some degree of relative dislocation at the fitted section between them, and the two can be fitted together while avoiding application of excessive force. This can help avoid damage to the cartridge 20 or driving base 40 caused by application of excessive force.

(3) Mounting of Fluid Feeder on Cartridge

After using a first sensor to confirm that a particular fluid feeder that houses somatic cells such as blood or skin cells is that of a specified person, the robot 50 grips the fluid feeder and connects it to the culture side supply plug 24 on the cartridge 20. Just before gripping, the first sensor is used to measure the position and posture of the fluid feeder, while the first sensor is also used to measure the position and posture of the culture side supply plug 24 just before connection, thus allowing correction of the prior taught position and posture of the robot 50 at the target location. The force control described above may also be carried out simultaneously.

(4) Confirming Operation of Driving Base by Sensor

Driving of the driving base 40 will cause changes in the liquid level in the fluid feeder, changes in the liquid level in the culture medium tank 28 of the cartridge 20, changes in the liquid level in the fluid storage tank and changes in the flow rate, and the robot 50 therefore confirms such liquid level changes using the first sensor. When the expected liquid level changes have not occurred, an alarm signal is posted to the host computer equipment indicating that some sort of problem has occurred.

(5) Confirming Separation of Inducing Source Cells by Sensor

As the inducing source cells (for example, monocytes, fibroblasts or somatic stem cells) are separated from the somatic cells such as blood or skin in the fluid storage tank, this causes a border to appear between the supernatant layer and the precipitated layer, and the robot 50 can confirm the location of the border using the first sensor. Since the expected amounts of supernatant layer and precipitated layer are known, it can be judged whether or not a phenomenon corresponding to a reference layer change has definitely occurred. When the expected layer change has not occurred, an alarm signal is posted to the host computer equipment indicating that some sort of problem has occurred.

(6) Mixing and Confirmation of Inducing Factors by Sensor

The robot 50 uses the first sensor to mount a fluid feeder that houses inducing factors (such as Sendai virus including the four Yamanaka genes, or reprogramming factors) onto a supply plug 24 of the cartridge 20. Intake and discharge of the fluid feeder are combined to draw in the inducing cell isolate to the fluid feeder side (mixing the inducing cell isolate with the inducing factor), and to then discharge the entire fluid into the cartridge 20. Since precise control is essential, the robot 50 uses the first sensor to constantly monitor liquid level changes and the flow rate in the fluid feeder. Since the expected liquid level changes and flow rates corresponding to intake and discharge of the driving units 41 for the fluid feeder are known, as are their speeds, it can be judged whether or not a phenomenon corresponding to a reference liquid level change has definitely occurred. When the expected changes have not occurred, an alarm signal is posted to the system end indicating that some sort of problem has occurred. Mixing and confirmation of the inducing factors may also be carried out in different fluid storage tanks and culture tanks.

(7) Color Tone Analysis of Culture Medium pH by Sensor

While the culture medium is being circulated, the first sensor measures the color of the culture medium at a specific location of the culture medium side plate along the channel, and the pH value of the culture medium is determined in a non-contact manner by color tone analysis based on the information received at the sensor. The pH value of the culture medium varies as the cells grow, and if a change transition has occurred at an expected level and the pH value has reached a predetermined value, then it is judged that it is time to replenish with fresh culture medium.

(8) Measurement of Cells or Cell Mass by Sensor

A second sensor (for example, a camera or ultrasonic sensor comprising a high-magnification lens) is temporarily gripped and carried near the end-effector of the robot 50, and the number, sizes, shapes and density of the cells or cell mass in the culture side plate 22 of the cartridge 20 are measured. When the second sensor is a camera comprising a high-magnification lens it is necessary to take several images of a wider area than the camera visual field, and therefore an XYZ driving mechanism is attached to the second sensor to allow fine movement of the imaging location in the XYZ directions. Alternatively, instead of being fixed near the end-effector of the robot 50, the second sensor may be temporarily held by the hand of the robot 50 and brought near to a specific cartridge 20, temporarily linking the second sensor to the cartridge 20, so that the robot 50 can leave that location to carry out separate processing. The second sensor linked to the cartridge 20 performs measurement several times in the culture side plate 22 during fine movement of the sensor driven by the XYZ driving mechanism. Once measurement in the culture side plate 22 is complete, the robot 50 again grips the second sensor, releases the linkage between the cartridge 20 and second sensor, and carries the second sensor away. The robot 50 may also place the second sensor around the periphery of the robot 50.

(9) Quality Analysis of Cells or Cell Mass by Sensor

A third sensor (for example, a camera or ultrasonic sensor comprising a high-magnification lens) mounted near the end-effector of the robot 50 is used for detailed examination of the state of the cells or cell mass in the cartridge 20. By using the third sensor to determine the state of the cells or cell mass in detail, it is possible to recognize and judge whether or not the cell mass maintains the prescribed quality.

(10) Transport of Cartridge to Observation Station.

The robot 50 temporarily (for a short period of time on the order of several tens of seconds to several minutes) cuts the cartridge 20 off from the driving base 40, and moves it to the observation station (such as a microscope measuring stage) to allow observation with a microscope. Further detailed measurement of the cells or cell mass may also be carried out at the observation station. After completion of microscopic observation, the robot 50 returns the cartridge 20 to the original driving base 40 location and couples them together. The microscopic observation itself is carried out by a separate device at the observation station.

(11) Transport of Cell Suspension Sample to Observation Station

As an alternative, the robot 50 may use the culture medium side discharge plug 31 of the cartridge 20 to remove the cell suspension sample out of the fluid discharger, and transport the fluid discharger to the observation station to allow observation with a microscope while maintaining the closed system of the cartridge 20. After completion of the microscopic observation, the robot 50 discards the fluid discharger. The microscopic observation itself is carried out by a separate device at the microscopic observation station. Alternatively, the microscopic observation and other examinations may be carried out by persons in a separate room.

(12) Cutting Off Fluid Discharger from Cartridge and Freezing

After all of the cell production steps have been successfully completed, the cell suspension is injected into the fluid discharger and the robot 50 cuts off the fluid discharger from the cartridge 20, and transports the fluid discharger to a freezing station.

(13) Dealing with Driving Base Problems

When a problem has occurred with the driving base 40, such as failure of the motor to be properly driven, the cartridge 20 is removed from the driving base and moved to and mounted on a different usable driving base 40. The host computer equipment is appropriately notified, and the cell production steps are continued as appropriate in the cartridge 20 by the driving base 40 that has been newly combined with the cartridge 20.

(14) Confirmation of Cartridge State by Sensor

When the series of cell production steps have been completed in the cartridge 20, the first sensor is used to continuously measure the state of predetermined locations in the cartridge 20 such as the channel, fluid storage tank and culture side plate 22. The information obtained for each location is used to comprehensively recognize and assess whether these locations are in their proper states, or whether some problem has occurred.

(15) Confirming State of Driving Base by Sensor

When the series of cell production steps have been completed in the cartridge 20 and the cartridge 20 has been removed by the robot 50, the first sensor is used to continuously measure the state of the motor, solenoid valve and sensor in the driving base 40 coupled with the cartridge 20, or the state of the periphery around the driving base 40. Based on the information obtained at each location, it is comprehensively recognized and assessed whether each location is in the proper state, or whether some problem has occurred such as a device malfunction or fluid leakage from the cartridge 20 side.

4. Computer System Conducting On-Demand Control

Because cell production entails variation in the product itself, the computer system of this example does not have a system control along a fixed flow, but rather a plurality of program modules are provided beforehand which comprise a process flow divided into small functional units, with the program modules being operated on-demand. Program modules are largely classified into two types. One type consists of robot program modules that involve operation of a robot 50 (hereunder referred to as "RPM"), and the other consists of closed cell production device program modules that do not involve operation of a robot 50, but rather operation of fluid machinery in individual closed cell production devices 10 and measurement by a sensor (such as a camera, flow meter and thermometer) (hereunder referred to as "IPM").

Figure 9:
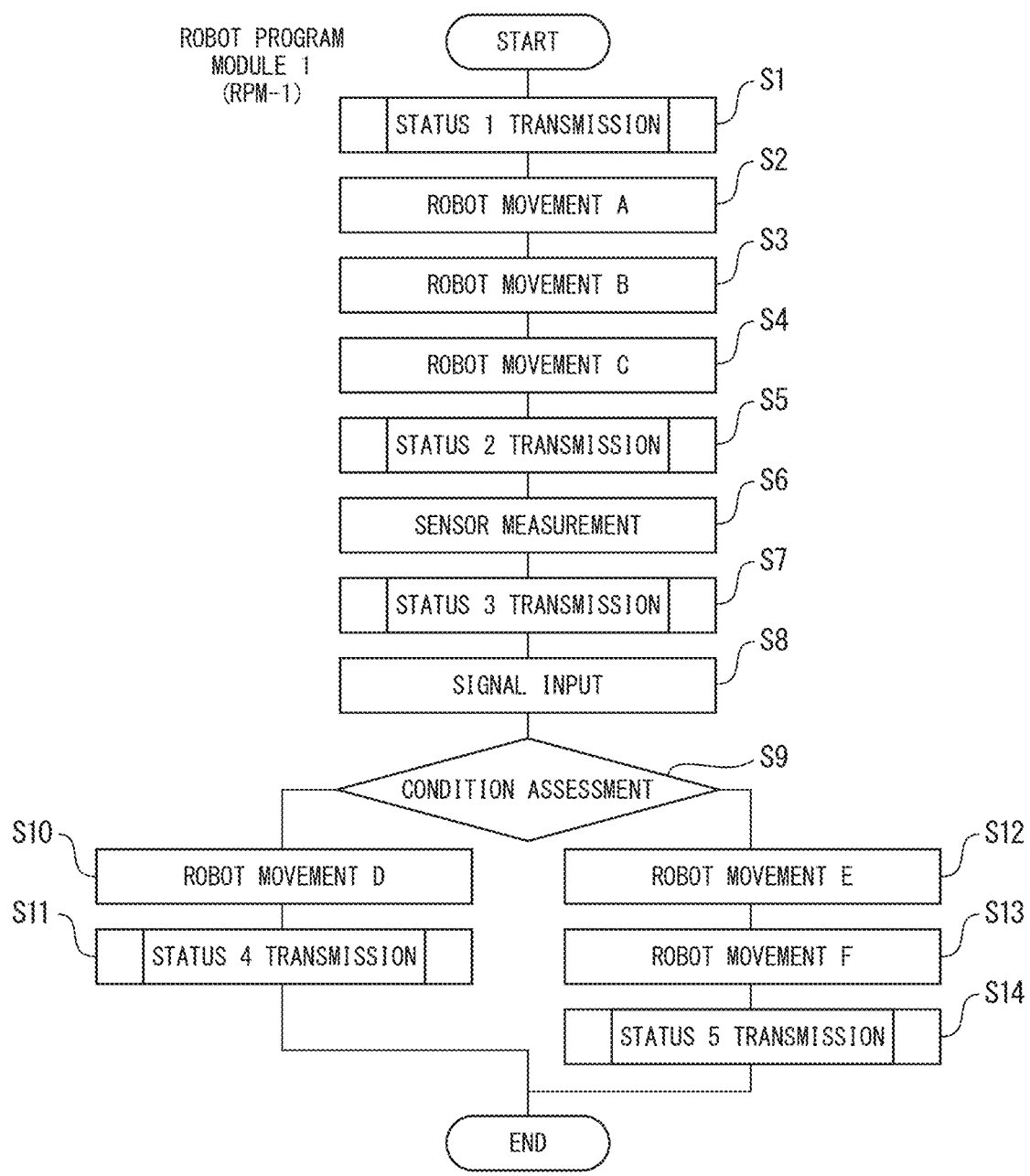
FIG. 9 is a flow chart showing an example of a robot program module.

FIG. 9 shows a flow chart for RPM-1. RPM-1 is a simplified conceptual depiction of an actual RPM type with implementation of a robot 50 being operated by running of the RPM-1. The RPM-1 is an example of a program module that conducts robot movement without necessarily requiring a sensor, with the following being typical.

a) Carrying of materials in and out of the cell production area b) Attachment and detachment of cartridges to driving bases c) Attachment and detachment of fluid feeders or fluid dischargers to cartridges d) Transport of cartridges to an observation station e) Transport of cell suspension samples to an observation station f) Cutting off of fluid dischargers from cartridges and freezing g) Dealing with driving base problems The following is an example of processing carried out by an RPM-1.

(Step S1) When the RPM-1 is called by a high-level program, a status 1 signal is outputted indicating that the RPM-1 has been called by the high-level program.

(Steps S2 to S5) Operation A, operation B and operation C are executed by the robot and a status 2 signal is outputted indicating that the operation has been properly completed.

(Steps S6 to S7) The state around the robot is measured by a predetermined sensor, and the measurement results are outputted as a status 3 signal.

(Step S8) The signals for the robot are inputted from an external device.

(Step S9) Conditions are assessed based on the content of the inputted signals, and the flow of program execution branches depending on the assessment results.

(Steps S10 to S11) When the flow of program execution is along one path, operation D is carried out by the robot and indication of proper completion of operation D is subsequently outputted as a status 4 signal.

(Steps S12 to S14) When the flow of program execution is along the other path, operation E and operation F are carried out by the robot and indication of proper completion of operations E and F is subsequently outputted as a status 5 signal. This completes processing by the RPM-1.

Figure 10:
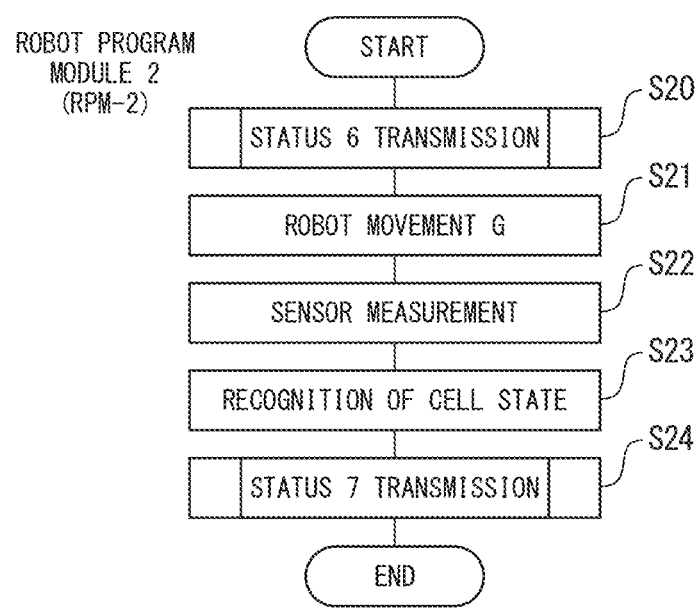
FIG. 10 is a flow chart showing an example of a robot program module.

FIG. 10 shows a flow chart for RPM-2. RPM-2 is a simplified conceptual depiction of an actual RPM type with implementation of a robot 50 being operated by running of the RPM-2. The RPM-2 is a program module that conducts robot movement using a sensor, with the following being typical.

h) Confirming state of driving bases by sensors i) Confirming operation of driving bases by sensors j) Observing interior of closed cell production devices by sensors k) Confirming cartridge states by sensors The following is an example of processing carried out by an RPM-2.

(Step S20) When the RPM-2 is called by a high-level program, a status 6 signal is outputted indicating that the RPM-2 has been activated.

(Step S21) The sensor is moved to a predetermined location near the culture side plate by robot movement G.

(Step S22) Measurement is carried out by the sensor.

(Step S23) The cells are detected based on information obtained from the sensor, and the number, density, sizes and shapes of the cells or cell masses are recognized.

(Step S24) The information relating to the cells in the culture side plate that has been recognized in all of the steps is outputted as a status 7 signal. The information signal that has been sent is also recorded in a data server for traceability, as described below.

Figure 11:
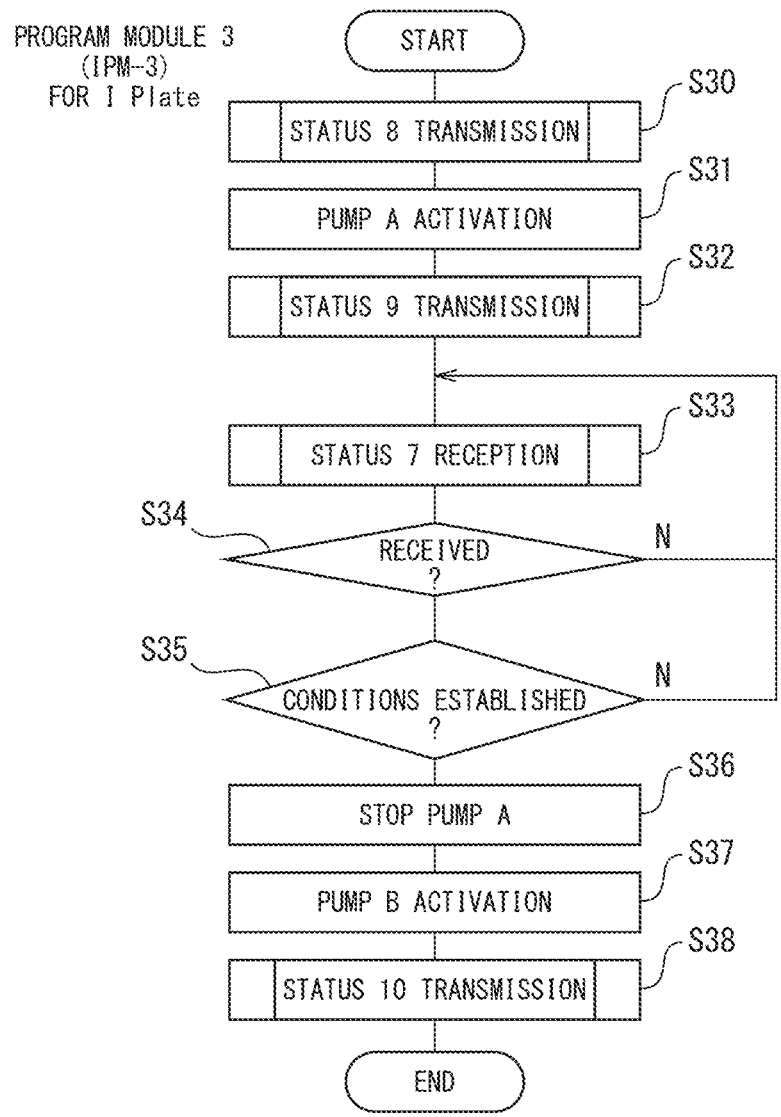
FIG. 11 is a flow chart showing an example of a closed cell production device program module.

FIG. 11 shows a flow chart for IPM-3. IPM-3 is a simplified and conceptual representation of an actual IPM, in which an actual closed cell production device 10 (with coupling of a cartridge 20 and driving base 40) is operated by execution of IPM-3. IPM-3 is a program module that carries out driving of a driving base and branching control based on the observation results from a sensor.

The following is an example of processing carried out by an IPM-3.

(Step S30) When the IPM-3 is called by a high-level program, a status 8 signal indicating that the IPM-3 has been activated is outputted first.

(Step S31) Activation of a pump A is then initiated to cause circulation of the culture medium on the back side of the culture side plate.

(Step S32) A status 9 signal is outputted indicating that the pump A has been activated.

(Step S33) It is then checked whether or not a status 7 has been received. Status 7 is sent by processing in the RPM-2, and the transmitted data is recorded in a data server for traceability as mentioned above, and is delivered to the IPM-3.

(Step S34) It is judged whether or not the status 7 has been received in the previous step, and if it has not been received, then step S33 is repeated. If it has been received, then operation proceeds to the next step.

(Step S35) It is judged whether or not predetermined conditions have been satisfied based on the information relating to cells in the culture side plate, which is included in the received status 7. The conditions include whether or not the average size of all of the recognized cells is above a predetermined value. If the conditions are not satisfied, then step 33 is repeated. If it has been received, then operation proceeds to the next step.

(Step S36) The pump A is stopped.

(Step S37) Activation is initiated for the pump B that serves to send the cell suspension in the culture side plate to the next step.

(Step S38) A status 10 signal is outputted indicating that activation of the pump B has been initiated.

By linking a plurality of different program modules of this kind, it is possible to observe the state of the cells or cell mass in the closed cell production device by the sensor, and to proceed to the cell production step in the closed cell production device based on the observation results. The stage that has been reached among the cell production steps with the closed cell production device can be assessed by whether or not the liquid volume in the fluid storage tank, the amount of supernatant liquid in the fluid storage tank, and the numbers and sizes of the cells or cell masses in the culture side plate have reached predetermined values. The values for each state are measured by a sensor such as a camera, and the measurement results are sent as feedback to the host computer equipment. An appropriate program module is activated depending on assessment by the host computer equipment based on the feedback information.

A step of status transmission to the various locations is incorporated into the program module beforehand, in order to record a log of operations carried out by the robot and closed cell production devices. Signal transduction is carried out, in other words. The status transmission step may be, specifically, handling of input/output signals with an external device, output of data to another computer via Ethernet™ communication or wireless communication, or access to a data server or a cloud system.

Figure 12:
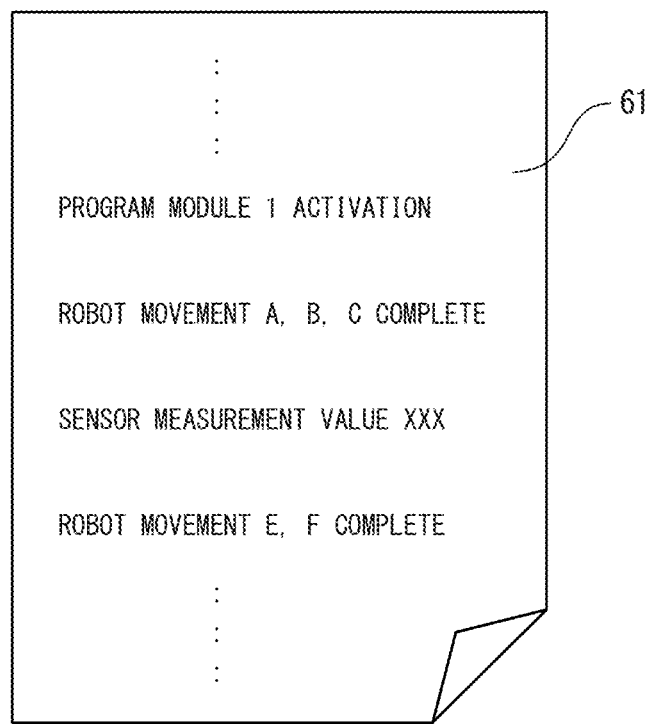
FIG. 12 is a diagram showing an example of information outputted and recorded by status transmission processing in a program module.

FIG. 12 conceptually shows recorded information 61 outputted by processing of status 1 transmission to status 5 transmission in a program module. In FIG. 12, the information appears as printed characters on a page, but it may also be electronic data stored in a data server or cloud server. The recorded information 61 may be one among other types of recorded information for traceability of specific cell production operations, and the recorded information 61 allowing tracking of cell production, such as indicating that robot movement E and robot movement F has been executed instead of robot movement D, for example. The information may also include date and time information.

The recorded information 61 indicates the manner and order in which the cell production steps have been carried out, and if an SOP is established beforehand, then comparison of the record of the actually performed steps may be compared with the SOP to determine whether they match, or allowing assessment of their differences if they do not match and whether or not the differences are within an allowable range. The assessment is carried out separately using several different types of sensors to eliminate bias in the assessment.

In this cell production system, a plurality of closed cell production devices (for example, 100×4=400) are controlled in parallel, and since the timing for initiating the cell production step in each closed cell production device is not necessarily the same as the other closed cell production devices, and differences also exist in the speed of progression of the cell production steps in each closed cell production device, there will be different levels of cell production in each closed cell production device. Since for a closed cell production device it is necessary for additional mounting of materials such as syringes, vials and infusion bags during the course of cell production, a status transmission step may also be provided for supply of the necessary materials during processing flow in the IPM-3 described above, for example, and the status may be received by a high-level program and a separate program module activated to supply the necessary members with a shuttle, for example. This will allow the materials required for each closed cell production device to be appropriately supplied in an on-demand manner to an area near the closed cell production device. In other words, the "Just In Time" system control is carried out in which only the required articles are supplied to the necessary locations in a timely manner.

Figure 13:
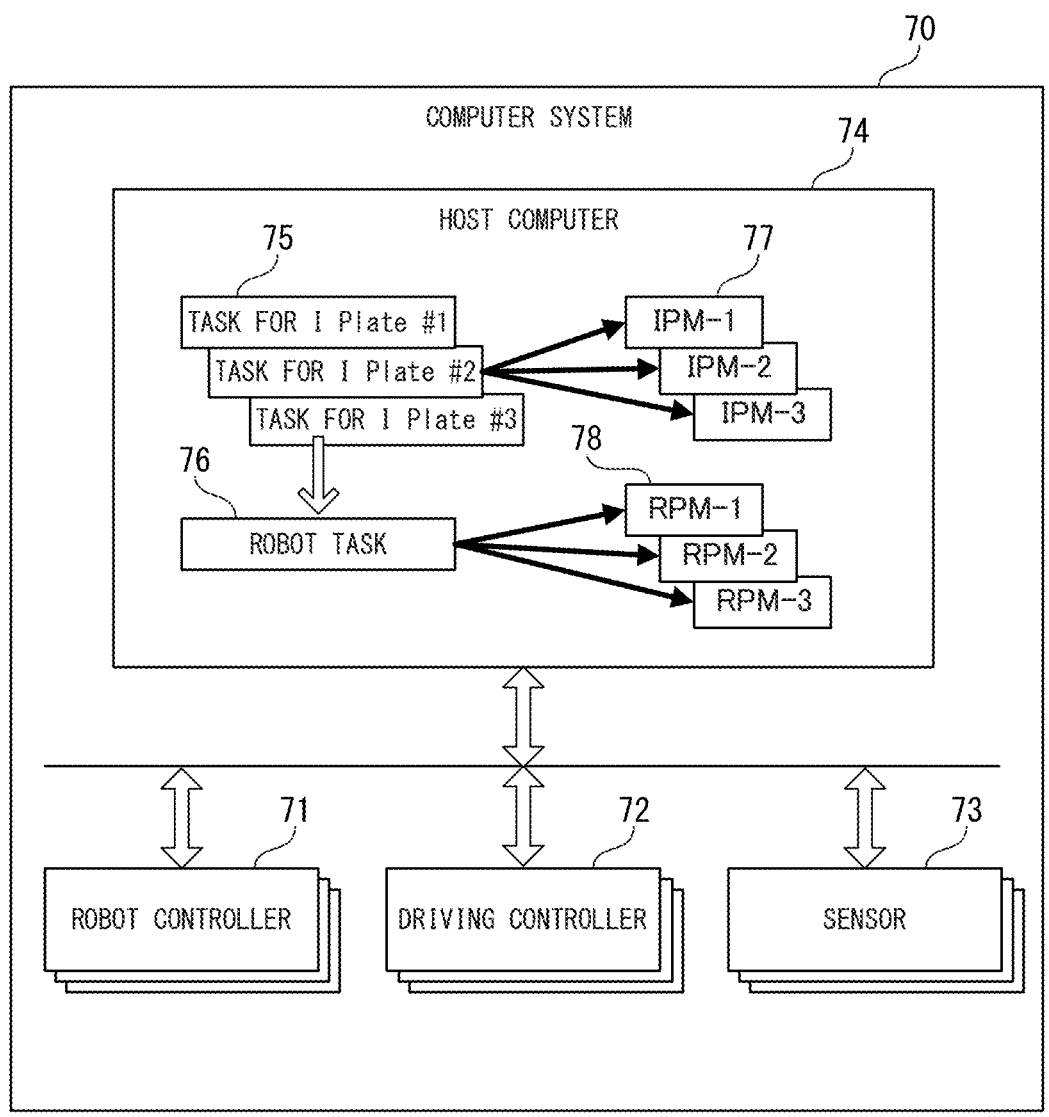
FIG. 13 is a block diagram showing an example of a computer system that carries out on-demand control.
Figure 14A:
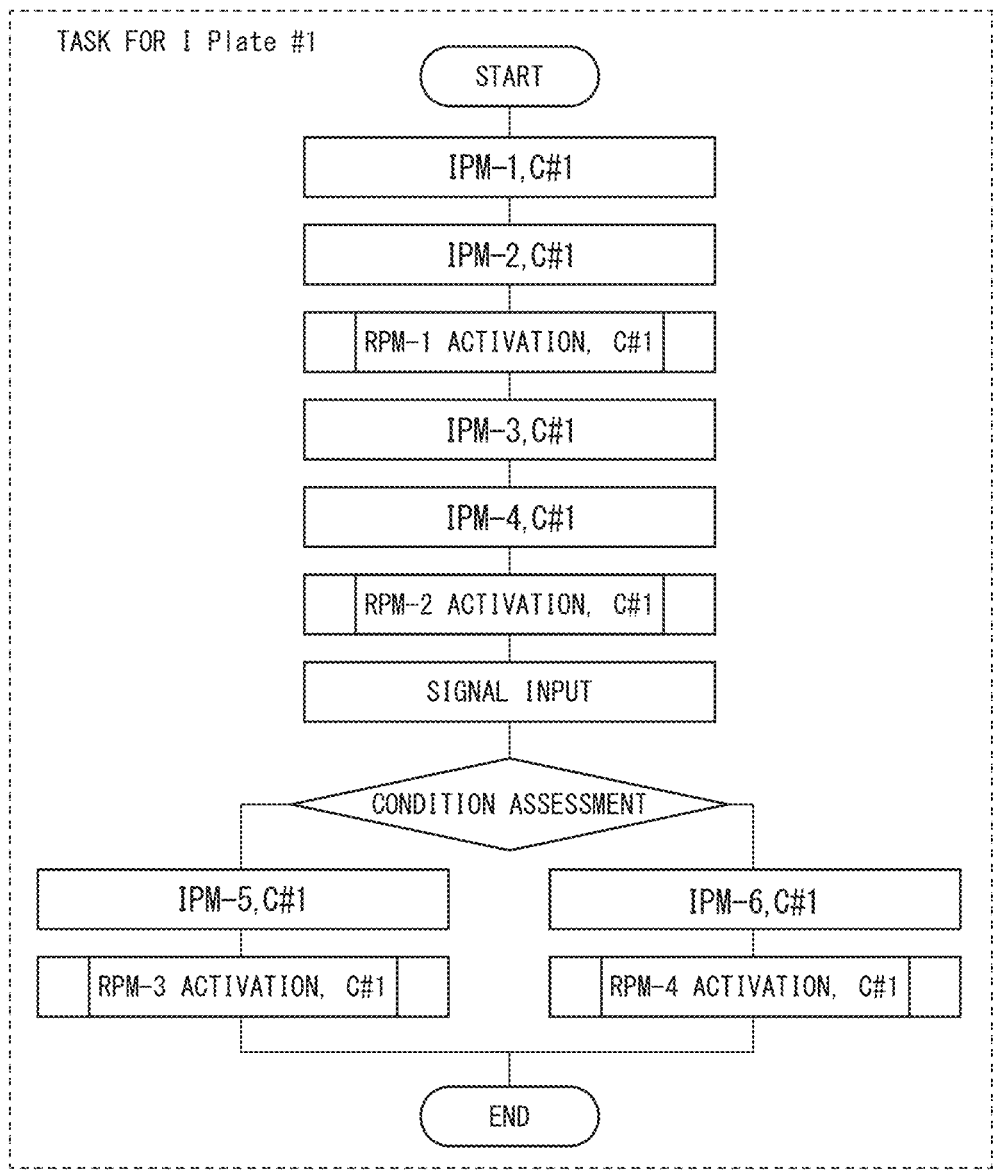
FIG. 14A is a flow chart for a closed cell production device task.
Figure 14B:
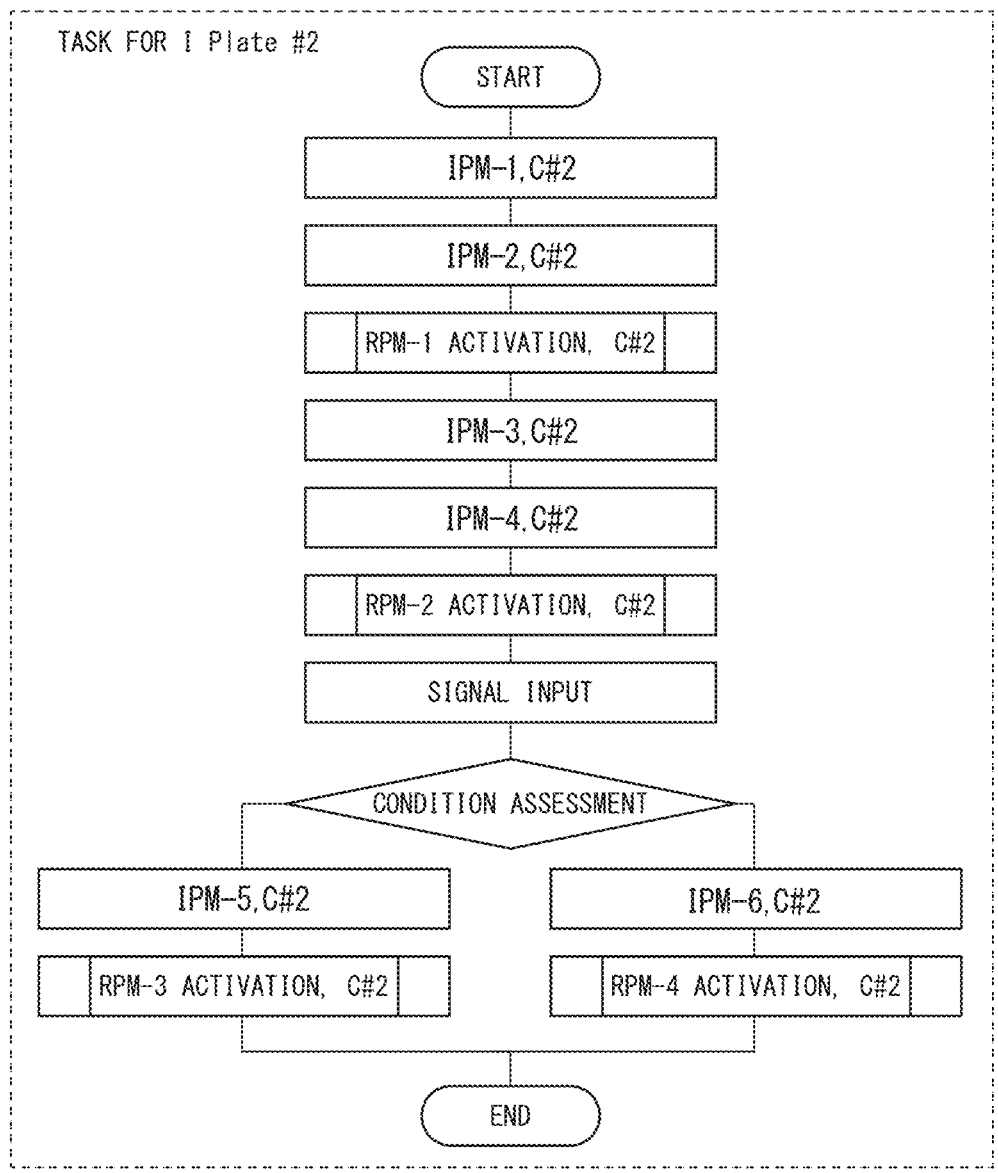
FIG. 14B is a flow chart for a closed cell production device task.
Figure 14C:
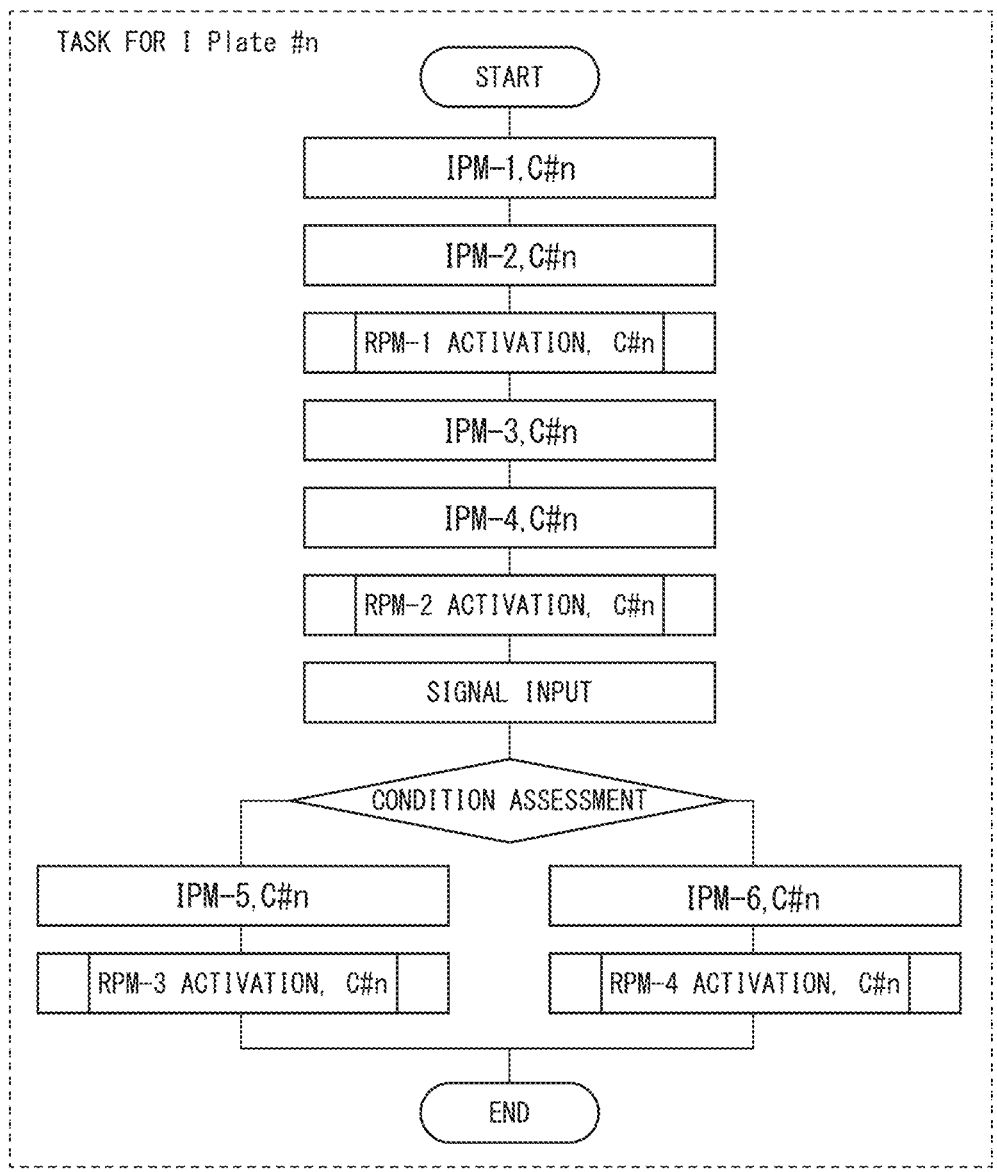
FIG. 14C is a flow chart for a closed cell production device task.

FIG. 13 shows an example of a computer system that carries out on-demand control. In general, the computer system 70 comprises one or several robot controllers 71 respectively controlling one or several robots, a driving controller 72 that controls driving of a plurality of closed system production devices, various sensors 73 such as cameras, and one host computer 74 that supervises and controls the entire cell production system. The robot controllers 71, driving controller 72, sensors 73 and host computer 74 are connected in a mutually communicating manner via a wired or wireless network.

In the host computer 74, n number of closed cell production device tasks 75 are generated corresponding in a one-to-one manner with n number of closed cell production devices (referred to here as "I Plates", i.e. I Plate #1, I Plate #2, . . . I Plate #n). A "task" is a program process or thread started on a multitasking operating system, for example. A robot task 76 is also generated corresponding to the actual robot (one in this case). All of the tasks are executed in parallel in a time sharing manner. The robot task 76 carries out communication in a many-to-one manner with the plurality of closed cell production device tasks 75 corresponding to the requests for closed cell production device tasks 75. The communication can be carried out by inter-process communication or inter-thread communication, but for a computer system in which robot tasks 76 are carried out by robot controllers 71, Ethernet™ communication or wireless communication is used. The closed cell production device tasks 75 activate one IPM from among a plurality of different previously prepared IPMs 77, requesting the robot task 76 to activate one RPM from among a plurality of different previously prepared RPMs 78.

FIG. 13A to FIG. 13C show the flow charts for different closed cell production device tasks 75. Each task has the same configuration. In the step labeled [IPM-*, C#*] in the closed cell production device task 75, the aforementioned IPM is called and activated. When the IPM is called, however, it is important to indicate the closed cell production device to which the processing is targeted, and this indication is represented as C#*. For example, C#1 indicates processing for I Plate #1, and C#n indicates processing for I Plate #n. Each IPM acts for a physically different closed cell production device as indicated, and operates the closed cell production device.

Since the closed cell production device tasks 75 run with several (1 to n) in parallel, it is possible for several of the same IPMs, such as IPM-1, to be executed simultaneously depending on the timing. Since the C#* indication will differ in such cases, this creates a condition in which physically different closed cell production devices move by IPM-1 devices called from separate tasks.

In the step labeled [RPM-* activation, C#*] for the closed cell production device task 75, the robot program module is not called but rather communication takes place between the closed cell production device task 75 and robot task 76 that actually carry out that step, and activation of RPM-* is requested for the robot task 76. Since it is important which closed cell production device is the target of robot movement by the request, it is indicated as C#*. Only the activation request is performed in this step, while processing flow for the closed cell production device task 75 proceeds forward. Specifically, when the step [PRM-1, C#*] is carried out, processing immediately proceeds to the following step [IPM-3, C#*].

Since several (1 to n) closed cell production device tasks 75 run in parallel, multiple RPM-* activation requests from different closed cell production device tasks 75 can potentially overlap. However, since there is one robot task 76 and actual robot, activation requests cannot take place simultaneously and execution takes place in first-come, first-serve order. Multiple overlapping RPM-* activation requests are controlled in a First In, First Out (FIFO) manner by processing generally referred to as "queueing" in common computer systems.

Figure 15:
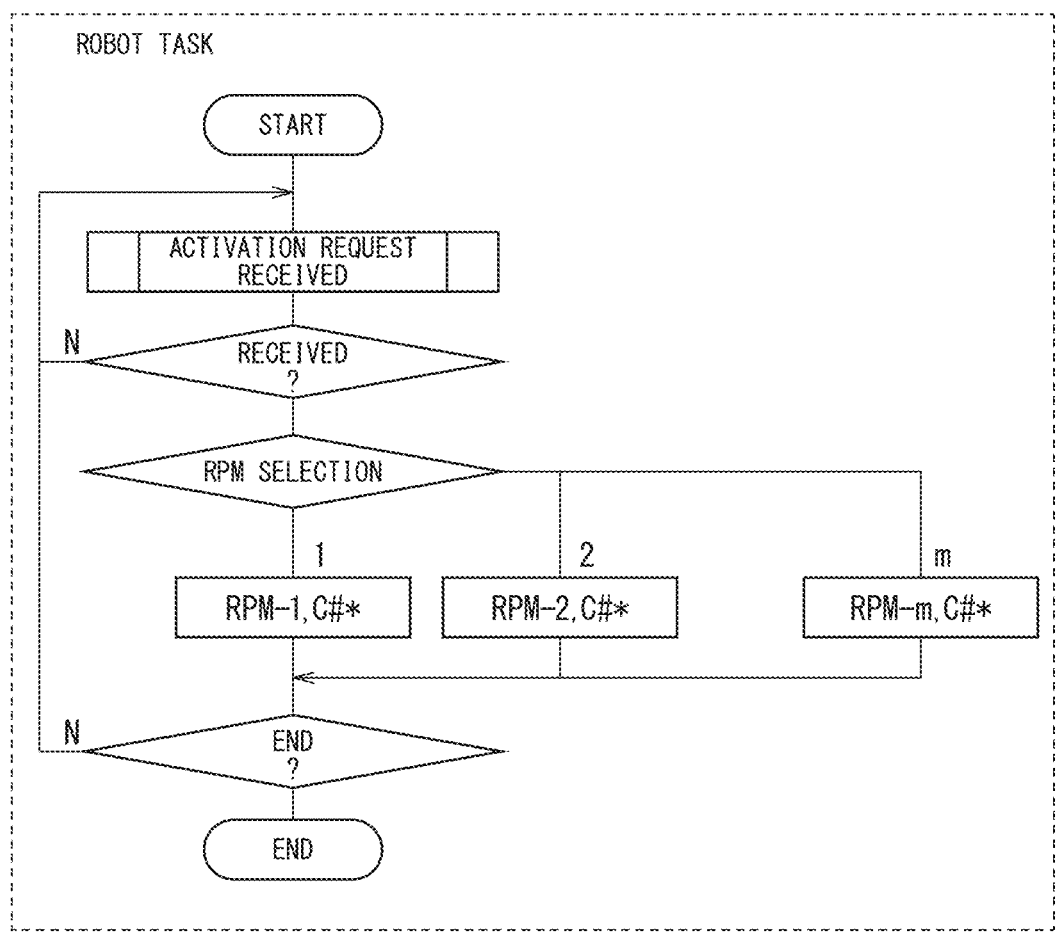
FIG. 15 is a flow chart for a robot task.

FIG. 15 shows a flow chart for a robot task 76. In this example of a robot task 76, when an RPM-* activation request has been received from a given closed cell production device task process, the appropriate RPM (1 to m from among m types in this case) is called and executed based on the information for the designated RPM-* number and the C#* flag indicating the target closed cell production device. The robot movement is thereby initiated for the designated closed cell production device and the prescribed operation is carried out.

5. Airflow Control System Against Possible Contamination

Figure 16A:
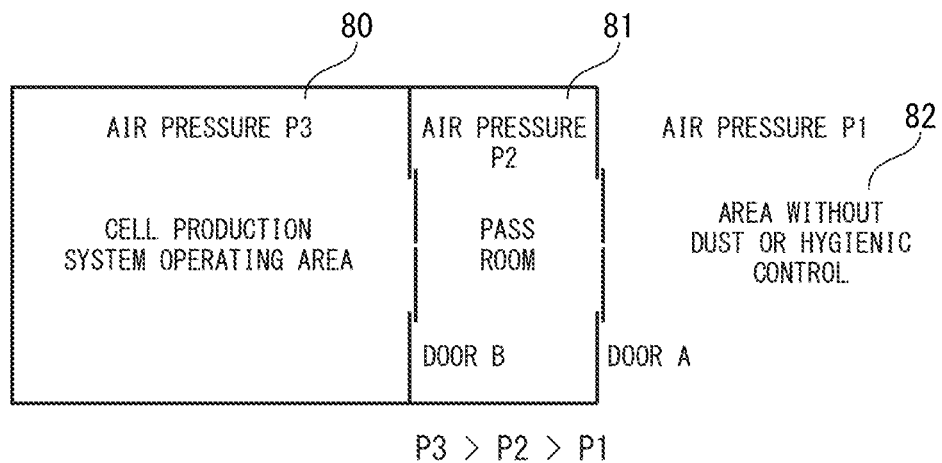
FIG. 16A is a plan view showing the operating area of a cell-type cell production system.
Figure 16B:
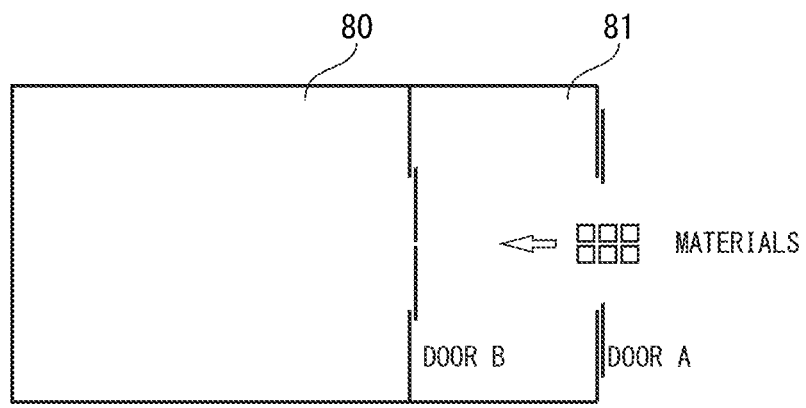
FIG. 16B is a plan view showing the operating area of a cell-type cell production system.
Figure 16C:
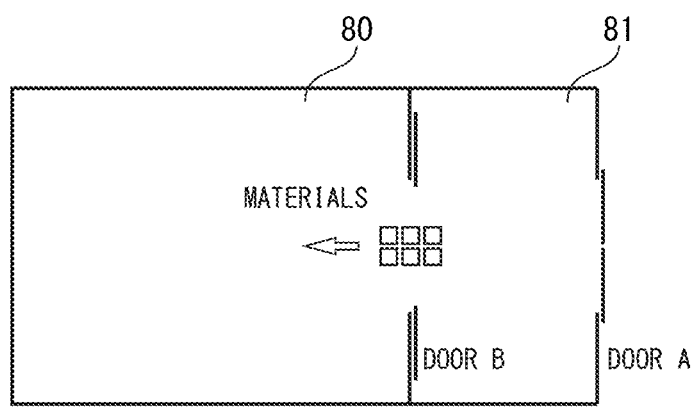
FIG. 16C is a plan view showing the operating area of a cell-type cell production system.

FIG. 16A to FIG. 16C show operating areas 80 in cell production systems. When materials are carried into and out of a space in which the closed cell production device and robot are situated during culturing, it is preferably through a pass box or pass room 81. This allows the flow of air to be controlled even if potential contamination occurs such as when the closed system has been breached, thus preventing episodes of air leakage.

Using these diagrams as examples, the cell production system is divided into an operating area 80, pass room 81 and other areas 82, the flow of air between the spaces is partitioned by shielding doors, and an appropriate sequence is followed for carrying of materials into the operating area of the cell production system.

Each area may also be regulated with positive/negative air pressure control, as shown in FIG. 16A. For the purpose of the disclosure, the configuration may also be one without special air pressure control in each of the areas. Operation control for door A and door B will prevent unwanted dust from being blown into the operating area of the cell production system.

When materials are being carried in, first the door A is opened and the materials are carried into the pass room 81, as shown in FIG. 16B. Dust adhering to the materials may also be blown off during this time by air blowing. Disinfection or sterilization may also be carried out by ethanol spraying, UV irradiation or hydrogen peroxide.

Next, as shown in FIG. 16C, the door A is closed and door B is opened, and the materials are carried into the area in which the cell production system is operating. After carrying in the materials, door B is closed, completing the series of carry-in sequence steps. When used materials are carried outside, the order of opening and closing the doors is reversed. Since cell production itself is carried out in the closed cell production device, shielding of air in each area does not need to be as strict as a CPC (Cell Processing Center).

Even if a maintenance worker should enter into the cell production area, this would occur through the pass room 81. Different pass rooms and different routes may also be provided as the carrying-in and carrying-out routes for materials to and from the cell production area, and the routes for entering and exiting of maintenance workers. Since a large volume is expected for the primary stock of materials being carried in and carried out, the pass room 81 may also be equipped with an automated storage location. When the material stock volume is large, the robot may manage the inventory of materials carried in and carried out, instead of a large-scale apparatus such as an automated storage location.

Figure 17:
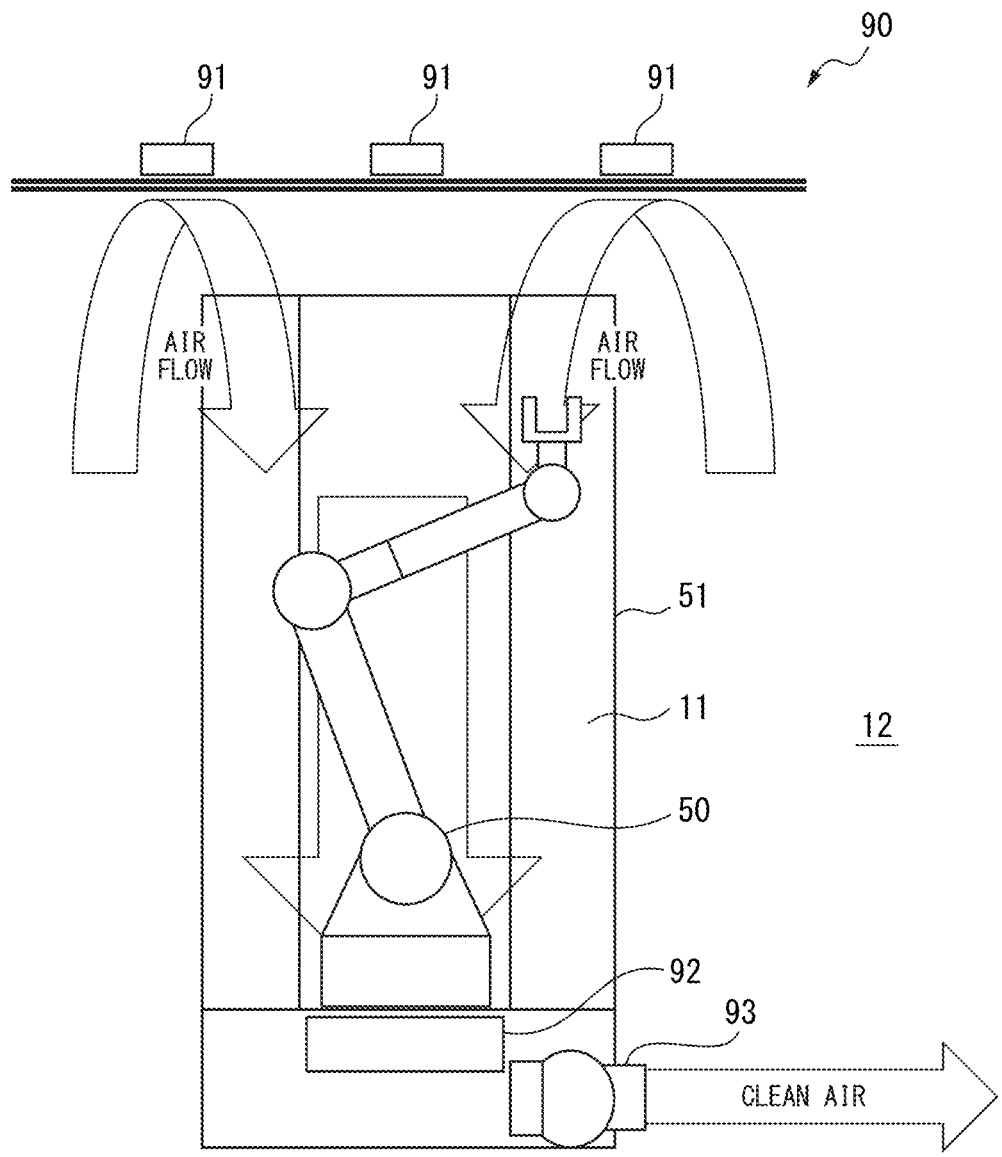
FIG. 17 is a side view of an example of an airflow control system.

FIG. 17 shows an example of an airflow control system 90. The airflow control system 90 of this example is applied to a cell-type cell production system. The cell 51 comprises a wall structure formed in a polygonal or circular shape, and an open top opening, the wall structure spatially separating the hazardous area side 11 and the safe area side 12. The robot 50 is disposed inside the cell 51, the robot 50 using an upwardly extending hand to transport materials 91 into the cell 51 from above the cell 51. A plurality of closed cell production devices (not shown) are also disposed in the wall structure of the cell 51. The airflow control system 90 is provided in the space of the hazardous area side 11, and controls downflow of air flowing from the region above to below the cell 51. The airflow control system 90 comprises a filtration filter 92 such as a HEPA filter situated below the cell 51, i.e. on its discharge side, and an exhaust fan 93 that discharges clean air provided by the filtration filter 92, to the outside of the cell 51. The following advantages are afforded by this type of airflow control system 90.

(1) It is possible to prevent potential biological contamination that may occur in the cell 51, even though the controlled area is a normal one that does not require a cleanroom.

(2) It is possible to prevent temperature irregularities and humidity irregularities in the cell 51 and to prevent temperature increase and humidity increase in the closed cell production device.

(3) It is possible to increase the degree of cleanliness in the background production environment since clean air is discharged out of the cell 51. The microparticle concentration can be controlled by setting the discharge airflow rate.

However, since the airflow control system 90 has a system configuration to deal with potential breaching of the closed system, the airflow control system does not necessarily need cleanliness control and ordinary air-conditioning without differential pressure regulation may be used. It should be noted that upflow control may be employed if the airflow control system 90 comprises a filtration filter 92 and an exhaust fan 93 on the discharge side.

6. Operational Features

The operational features will now be described.

6-1. Traceability

Information data for all of the actions in the cell production process (such as activity logs for the processing flow in the activated task program and program module) and the sensor measured values, are aggregated and recorded in a host computer. For traceability, the following information, including the information mentioned above, are associated and stored in a database.

(1) Personal information for the cell creators (name, age, date of birth, blood type, nationality, address)
(2) Individual genomic information
(3) Individual family structure
(4) Individual case history, medical history and past/present treatment history
(5) Blood collection location, date and time and blood collection volume used for cell creation
(6) All logs for cell creation process (status information outputted by robot program module, status information outputted by program module for closed system production device, etc.)
(7) Results of comparing all logs with previously prepared SOP, and assessment of comparison
(8) Inspection results for created cells
(9) Storage location and anticipated storage period for created cells.
(10) Stored cell usage history 6-2. Methods for Identification Information Control and Production Recording ID control and production recording may be carried out by any of the following methods.

(1) A system in which a host computer carries out centralized management in real time
(2) A system which records in IC chips embedded in the individual closed cell production devices, and subsequently aggregates in a managing server
(3) A system in which unique IDs are assigned beforehand to all materials related to cell production, with the respective IDs being attached to each material in the form of a two-dimensional barcode, three-dimensional barcode, IC chip or the like, and the IDs are read by a sensor such as a camera just before being used in the respective closed cell production devices, and sent to the host computer or IC chip.

6-3. Closed System Production Device Control Method

Each of the closed system production devices is controlled by one of the following methods.

(1) Several pumps and several sensors in a single closed system production device are controlled by a single control system (the closed system production devices and control systems are in a one-to-one relationship).
(2) A network system such as a FIELD System™ controls the pumps and multiple sensors included in N number of closed system production devices.

The software for this embodiment may be provided from a storing non-temporary recording medium or CD-ROM that is readable by a computer. The embodiments described herein are not intended to limit the scope of the invention, and it will be recognized that various modifications may be made within the scope of the Claims as laid out below.

REFERENCE SIGNS LIST

1 Cell production system
10 Closed cell production device
20 Cartridge
21 Culture component permeating member
22 Culture side plate
23 Culture medium side plate
24 Culture side supply plug
25 Culture side discharge plug
26 Culture medium holding layer
27 Culture medium channel 28 Culture medium tank
29 Fluid machinery
30 Culture medium side supply plug
31 Culture medium side discharge plug
32 Window
40 Driving base
41 Driving unit
42 Drive holding member
43 Outside air blocking member
50 Robot
51 Cell
52 Material transport mechanism
53 Shuttle
54 Travel axis rail
55 Slider
56 Opening
57 Shutter
60 Wall structure
61 Recorded information
70 Computer system
71 Robot controller
72 Driving controller
73 Sensor
74 Host computer
75 Closed cell production device task
76 Robot task
77 Closed cell production device program module
78 Robot program module
80 Cell production system operating area
81 Pass room
82 Other area
90 Airflow control system
91 Material
92 Filtration filter
93 Exhaust fan

The invention claimed is:

1. A cell production system, comprising:
a robot that assists in cell production,
a plurality of cell production devices which includes a closed culture vessel and which are affected by the robot in a one-to-many manner, and
a computer system which has a plurality of cell production device tasks to be executed in parallel, and a robot task in communication with the plurality of cell production device tasks in a many-to-one manner, wherein
the robot task activates at least one program module from among a plurality of different robot program modules in response to requests by the plurality of cell production device tasks,
each of the plurality of cell production devices comprises
a removable cell production cartridge, and
a driving base that drives the removable cell production cartridge, and
wherein the plurality of different robot program modules includes a program module for at least one of the following robot movements:
a) carrying of materials in and out of a cell production area,
b) attachment and detachment of the removable cell production cartridges to the driving bases,
c) attachment and detachment of fluid feeders or fluid dischargers to the removable cell production cartridges,
d) transport of the removable cell production cartridges to an observation station,
e) transport of cell suspension samples to the observation station,
f) cutting off of the fluid dischargers from the removable cell production cartridges and freezing,
g) dealing with driving base problems,
h) confirming a state of the driving bases by sensors,
i) confirming operation of the driving bases by sensors,
j) observing an interior of the plurality of cell production devices by sensors, and
k) confirming cartridge states by sensors.

2. The cell production system according to claim 1, wherein
a cell production device task of the plurality of cell production device tasks or a robot program module of the plurality of different robot program modules comprises
a step of performing an action on a cell production device of the plurality of cell production devices according to a previously established Standard Of Process,
a step of performing an assessment of whether or not the action has been carried out according to the previously established Standard Of Process and whether or not an anticipated result has been obtained, and
a step of recording the action and assessment.

3. The cell production system according to claim 2, further comprising:
a plurality of different sensors, with the assessment being carried out using the plurality of different sensors.

* * * * *